(12) United States Patent
Zenz-Olson et al.

(10) Patent No.: US 12,414,765 B2
(45) Date of Patent: *Sep. 16, 2025

(54) FASTENER DELIVERY SYSTEM AND RELATED METHODS

(71) Applicant: ROTATION MEDICAL, INC., Memphis, TN (US)

(72) Inventors: Nathaniel Zenz-Olson, Blaine, MN (US); Nathaniel Tran, Lakeville, MN (US)

(73) Assignee: ROTATION MEDICAL, INC., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/642,000

(22) Filed: Apr. 22, 2024

(65) Prior Publication Data

US 2024/0268820 A1    Aug. 15, 2024

Related U.S. Application Data

(63) Continuation of application No. 16/934,977, filed on Jul. 21, 2020, now Pat. No. 11,986,181, which is a
(Continued)

(51) Int. Cl.
*A61B 17/068* (2006.01)
*A61B 17/02* (2006.01)
(Continued)

(52) U.S. Cl.
CPC ...... *A61B 17/0682* (2013.01); *A61B 17/0218* (2013.01); *A61B 17/0642* (2013.01);
(Continued)

(58) Field of Classification Search
CPC ............ A61B 17/0218; A61B 17/0642; A61B 17/068; A61B 17/0682; A61B 17/3421;
(Continued)

(56) References Cited

U.S. PATENT DOCUMENTS

| 511,238 A | 12/1893 | Hieatzman et al. |
| 765,793 A | 7/1904 | Ruckel |

(Continued)

FOREIGN PATENT DOCUMENTS

| AU | 2010256474 B2 | 12/2010 |
| CA | 2390508 A1 | 5/2001 |

(Continued)

OTHER PUBLICATIONS

International Search Report and Written Opinion for Application No. PCT/US2016/069292, 26 pages, dated Apr. 12, 2017.

*Primary Examiner* — Kankindi Rwego
(74) *Attorney, Agent, or Firm* — Seager, Tufte & Wickhem LLP

(57) ABSTRACT

A fastener delivery tool is disclosed. An example fastener delivery tool comprises a sheath assembly including a sheath and a position retention member and a retraction assembly including a cover and a retractor member. The cover includes a lumen extending therein. The fastener delivery tool also includes and a handle assembly coupled to a proximal end of the sheath assembly, the handle assembly including a housing and an actuation member. Further, the sheath assembly extends through the lumen of the cover and the retractor member is configured to move relative to the handle between a first position in which the sheath assembly is disposed within a distal portion of the cover and a second position in which the sheath assembly extends out of the distal portion of the cover. Additionally, actuation of the actuation member moves the retractor member from the first position to the second position.

18 Claims, 21 Drawing Sheets

Related U.S. Application Data continuation of application No. 15/394,350, filed on Dec. 29, 2016, now Pat. No. 10,758,228.

(60) Provisional application No. 62/273,890, filed on Dec. 31, 2015.

(51) Int. Cl.
*A61B 17/064* (2006.01)
*A61B 17/34* (2006.01)
*A61F 2/08* (2006.01)
*A61B 90/00* (2016.01)

(52) U.S. Cl.
CPC ............ *A61B 17/3421* (2013.01); *A61F 2/08* (2013.01); *A61F 2/0811* (2013.01); *A61B 2090/034* (2016.02); *A61B 2090/08021* (2016.02); *A61B 2217/005* (2013.01); *A61B 2217/007* (2013.01); *A61F 2/0805* (2013.01); *A61F 2002/0829* (2013.01); *A61F 2002/0858* (2013.01)

(58) Field of Classification Search
CPC ... A61B 90/03; A61B 90/08; A61B 2090/034; A61B 2090/08021; A61B 2217/005; A61B 2217/007; A61F 2/0811
USPC ......................................................... 606/219
See application file for complete search history.

(56) References Cited

U.S. PATENT DOCUMENTS

| | | |
|---|---|---|
| 1,728,316 A | 9/1929 | Von Wachenfeldt |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,154,688 A | 4/1939 | Matthews et al. |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,390,508 A | 12/1945 | Carleton |
| 2,397,240 A | 3/1946 | Butler |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,120,377 A | 2/1964 | Lipschultz et al. |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,740,994 A | 6/1973 | DeCarlo, Jr. |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,394,864 A | 7/1983 | Sandhaus |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,586,197 A | 5/1986 | Hubbard |
| 4,595,007 A | 6/1986 | Mericle |
| 4,610,251 A | 9/1986 | Kumar |
| 4,624,254 A | 11/1986 | McGarry et al. |
| 4,627,437 A | 12/1986 | Bedi et al. |
| 4,632,100 A | 12/1986 | Somers et al. |
| 4,635,634 A | 1/1987 | Santos |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | Mckinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |

(56) References Cited

U.S. PATENT DOCUMENTS

| | | |
|---|---|---|
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,439,468 A | 8/1995 | Schulze et al. |
| 5,441,502 A | 8/1995 | Bartlett |
| 5,441,508 A | 8/1995 | Gazielly et al. |
| 5,456,720 A | 10/1995 | Schultz et al. |
| 5,458,579 A | 10/1995 | Chodorow et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,185 A | 5/1996 | Soni et al. |
| 5,520,700 A | 5/1996 | Beyar et al. |
| 5,522,817 A | 6/1996 | Sander et al. |
| 5,538,297 A | 7/1996 | Mc Naughton et al. |
| 5,545,180 A | 8/1996 | Le et al. |
| 5,548,893 A | 8/1996 | Koelfgen et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,593,421 A | 1/1997 | Bauer |
| 5,601,573 A | 2/1997 | Fogelberg et al. |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,888 A | 8/1998 | Yoon |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,833,700 A | 11/1998 | Fogelberg et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | Dipoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,258,105 B1 | 7/2001 | Hart et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,342,057 B1 | 1/2002 | Brace et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,286 B2 | 7/2003 | Campin et al. |
| 6,599,289 B1 | 7/2003 | Bojarski et al. |
| 6,620,185 B1 | 9/2003 | Harvie et al. |
| 6,626,930 B1 | 9/2003 | Allen et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Muijs Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |

(56) References Cited

U.S. PATENT DOCUMENTS

| | | |
|---|---|---|
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,318 B2 | 9/2005 | Stenzel |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Friden |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,819,888 B2 | 10/2010 | Johanson et al. |
| 7,918,879 B2 | 4/2011 | Yeung et al. |
| 7,931,660 B2 | 4/2011 | Aranyi et al. |
| 8,034,076 B2 | 10/2011 | Criscuolo et al. |
| 8,114,101 B2 | 2/2012 | Criscuolo et al. |
| 8,197,837 B2 | 6/2012 | Jamiolkowski et al. |
| 8,292,853 B2 | 10/2012 | Hart et al. |
| 8,585,773 B1 | 11/2013 | Kucklick |
| 8,668,718 B2 | 3/2014 | Euteneuer et al. |
| 8,763,878 B2 | 7/2014 | Euteneuer et al. |
| 8,821,536 B2 | 9/2014 | Euteneuer et al. |
| 8,821,537 B2 | 9/2014 | Euteneuer et al. |
| 8,840,642 B2 | 9/2014 | Euteneuer et al. |
| 8,864,780 B2 | 10/2014 | Euteneuer et al. |
| 8,894,669 B2 | 11/2014 | Nering et al. |
| 8,920,464 B2 | 12/2014 | Euteneuer et al. |
| 9,005,224 B2 | 4/2015 | Euteneuer et al. |
| 9,027,819 B2 | 5/2015 | Euteneuer et al. |
| 9,033,201 B2 | 5/2015 | Euteneuer |
| 9,095,337 B2 | 8/2015 | Euteneuer et al. |
| 9,101,460 B2 | 8/2015 | Euteneuer et al. |
| 9,107,661 B2 | 8/2015 | Euteneuer et al. |
| 9,113,977 B2 | 8/2015 | Euteneuer et al. |
| 9,125,650 B2 | 9/2015 | Euteneuer et al. |
| 9,179,910 B2 | 11/2015 | Euteneuer et al. |
| 9,179,961 B2 | 11/2015 | Euteneuer et al. |
| 9,192,013 B1 | 11/2015 | van de Ven et al. |
| 9,198,750 B2 | 12/2015 | Van Kampen et al. |
| 9,198,751 B2 | 12/2015 | Euteneuer et al. |
| 9,204,940 B2 | 12/2015 | Euteneuer et al. |
| 9,247,978 B2 | 2/2016 | Euteneuer et al. |
| 9,259,220 B2 | 2/2016 | Euteneuer et al. |
| 9,271,726 B2 | 3/2016 | Euteneuer |
| 9,314,314 B2 | 4/2016 | Euteneuer et al. |
| 9,314,331 B2 | 4/2016 | Euteneuer et al. |
| 9,370,356 B2 | 6/2016 | Euteneuer et al. |
| 9,393,103 B2 | 7/2016 | Van Kampen et al. |
| 9,393,104 B2 | 7/2016 | Kampen et al. |
| 9,414,841 B2 | 8/2016 | Euteneuer et al. |
| 9,566,063 B2 | 2/2017 | Euteneuer et al. |
| 9,878,141 B2 | 1/2018 | Kucklick |
| 10,076,374 B2 | 9/2018 | Diduch et al. |
| 10,758,228 B2 * | 9/2020 | Zenz-Olson ........ A61B 17/3421 |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2002/0169465 A1 | 11/2002 | Bowman et al. |
| 2002/0188301 A1 | 12/2002 | Dallara et al. |
| 2003/0073979 A1 | 4/2003 | Naimark et al. |
| 2003/0125748 A1 | 7/2003 | Li et al. |
| 2003/0135224 A1 | 7/2003 | Blake, III |
| 2003/0212456 A1 | 11/2003 | Lipchitz et al. |
| 2004/0059416 A1 | 3/2004 | Murray et al. |
| 2004/0092937 A1 | 5/2004 | Criscuolo et al. |
| 2004/0138705 A1 | 7/2004 | Heino et al. |
| 2004/0167519 A1 | 8/2004 | Weiner et al. |
| 2004/0220574 A1 | 11/2004 | Pelo et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0055027 A1 | 3/2005 | Yeung et al. |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0038222 A1 | 2/2007 | Bhatnagar et al. |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |

(56) References Cited

U.S. PATENT DOCUMENTS

| | | |
|---|---|---|
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0139473 A1 | 6/2008 | Ladner et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2008/0312688 A1 | 12/2008 | Nawrocki et al. |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0121153 A1* | 5/2010 | To ............... A61B 17/3417 600/214 |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0211097 A1 | 8/2010 | Hadba et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0079627 A1 | 4/2011 | Cardinale et al. |
| 2011/0106154 A1 | 5/2011 | DiMatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer |
| 2012/0248171 A1 | 10/2012 | Bailly et al. |
| 2012/0316608 A1 | 12/2012 | Foley |
| 2013/0116708 A1* | 5/2013 | Ziniti ............... A61B 17/0485 606/144 |
| 2013/0153627 A1 | 6/2013 | Euteneuer et al. |
| 2013/0153628 A1 | 6/2013 | Euteneuer |
| 2013/0158554 A1 | 6/2013 | Euteneuer et al. |
| 2013/0158587 A1 | 6/2013 | Euteneuer et al. |
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245693 A1 | 9/2013 | Blain |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |
| 2013/0245774 A1 | 9/2013 | Euteneuer et al. |
| 2013/0304115 A1 | 11/2013 | Miyamoto |
| 2014/0188161 A1 | 7/2014 | Euteneuer et al. |
| 2014/0288593 A1 | 9/2014 | Euteneuer et al. |
| 2014/0358163 A1 | 12/2014 | Farin et al. |
| 2014/0371853 A1 | 12/2014 | Kampen et al. |
| 2015/0025630 A1 | 1/2015 | Euteneuer et al. |
| 2015/0112370 A1 | 4/2015 | Euteneuer et al. |
| 2015/0182326 A1 | 7/2015 | Euteneuer et al. |
| 2015/0230792 A1 | 8/2015 | Euteneuer et al. |
| 2015/0238190 A1 | 8/2015 | Euteneuer |
| 2015/0250477 A1 | 9/2015 | Euteneuer et al. |
| 2015/0272573 A1 | 10/2015 | Euteneuer et al. |
| 2015/0313705 A1 | 11/2015 | Euteneuer et al. |
| 2015/0320543 A1 | 11/2015 | Zenz-Olson |
| 2015/0327858 A1 | 11/2015 | Euteneuer et al. |
| 2015/0327975 A1 | 11/2015 | Euteneuer et al. |
| 2016/0030150 A1 | 2/2016 | Euteneuer et al. |
| 2016/0030157 A1 | 2/2016 | Euteneuer et al. |
| 2016/0051300 A1 | 2/2016 | Euteneuer et al. |
| 2016/0058535 A1 | 3/2016 | Euteneuer et al. |
| 2016/0073491 A1 | 3/2016 | Chen et al. |
| 2016/0100935 A1 | 4/2016 | Euteneuer et al. |
| 2016/0120538 A1 | 5/2016 | Westling et al. |
| 2016/0120542 A1 | 5/2016 | Westling et al. |
| 2016/0128693 A1 | 5/2016 | Euteneuer et al. |
| 2016/0135806 A1 | 5/2016 | Euteneuer |
| 2016/0256254 A1 | 9/2016 | Kucklick |
| 2016/0256258 A1 | 9/2016 | Euteneuer et al. |
| 2016/0262747 A1 | 9/2016 | Euteneuer et al. |
| 2016/0262780 A1 | 9/2016 | Kucklick |
| 2016/0296318 A1 | 10/2016 | Van Kampen et al. |
| 2016/0317147 A1 | 11/2016 | Euteneuer et al. |
| 2016/0317281 A1 | 11/2016 | Van Kampen et al. |
| 2016/0324616 A1 | 11/2016 | Zenz-Olson et al. |
| 2016/0361155 A1 | 12/2016 | Van Kampen |

FOREIGN PATENT DOCUMENTS

| | | |
|---|---|---|
| EP | 0142225 A1 | 5/1985 |
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 0589306 B1 | 8/1999 |
| EP | 1491157 A1 | 12/2004 |
| EP | 1559379 A1 | 8/2005 |
| EP | 1491157 B1 | 11/2008 |
| EP | 2030576 A2 | 3/2009 |
| EP | 2039316 A2 | 3/2009 |
| GB | 2154688 A | 9/1985 |
| GB | 2397240 A | 7/2004 |
| JP | 58188442 A | 11/1983 |
| JP | 2005586122 A | 3/2005 |
| JP | 2006515774 A | 6/2006 |
| JP | 2012514191 A | 6/2012 |
| JP | 2012528699 A | 11/2012 |
| WO | 8505025 A1 | 11/1985 |
| WO | 0176456 A2 | 10/2001 |
| WO | 0234140 A2 | 5/2002 |
| WO | 03032815 A2 | 4/2003 |
| WO | 2003105670 A2 | 12/2003 |
| WO | 2004000138 A1 | 12/2003 |
| WO | 2004062508 A1 | 7/2004 |
| WO | 2004093690 A1 | 11/2004 |

(56) References Cited

FOREIGN PATENT DOCUMENTS

| | | | |
|---|---|---|---|
| WO | 2005016389 | A2 | 2/2005 |
| WO | 2006086679 | A1 | 8/2006 |
| WO | 2007014910 | A1 | 2/2007 |
| WO | 2007030676 | A2 | 3/2007 |
| WO | 2007078978 | A2 | 7/2007 |
| WO | 2007082088 | A2 | 7/2007 |
| WO | 2008065153 | A1 | 6/2008 |
| WO | 2008111073 | A2 | 9/2008 |
| WO | 2008111078 | A2 | 9/2008 |
| WO | 2008139473 | A2 | 11/2008 |
| WO | 2009079211 | A1 | 6/2009 |
| WO | 2009143331 | A1 | 11/2009 |
| WO | 2010141872 | A1 | 12/2010 |
| WO | 2010141907 | A1 | 12/2010 |
| WO | 2011095890 | A2 | 8/2011 |
| WO | 2011128903 | A2 | 10/2011 |
| WO | 2013007764 | A2 | 1/2013 |
| WO | 2013119321 | A1 | 8/2013 |
| WO | 2018144887 | A1 | 8/2018 |

* cited by examiner

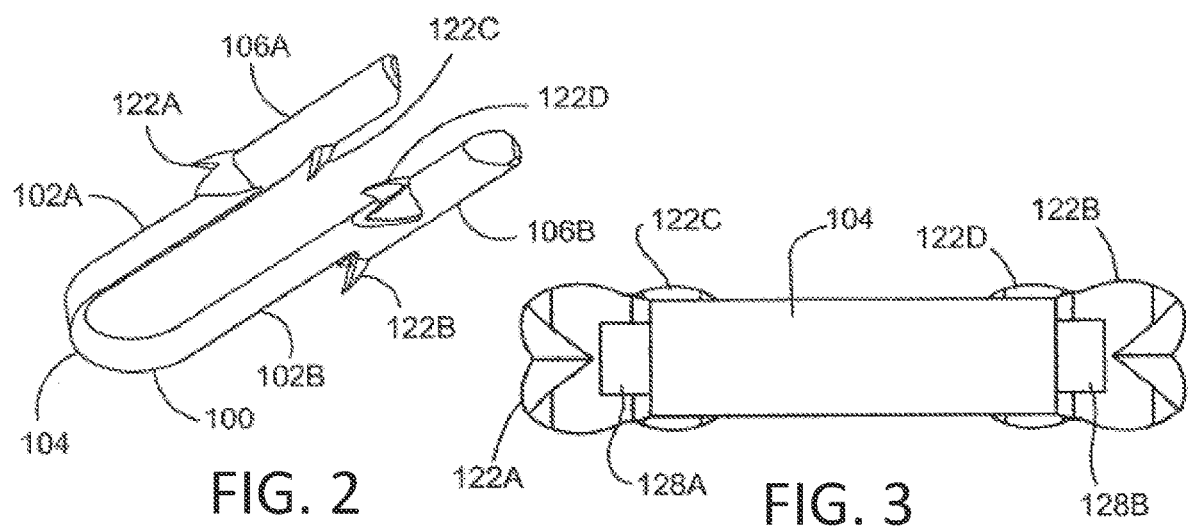
FIG. 2
FIG. 3
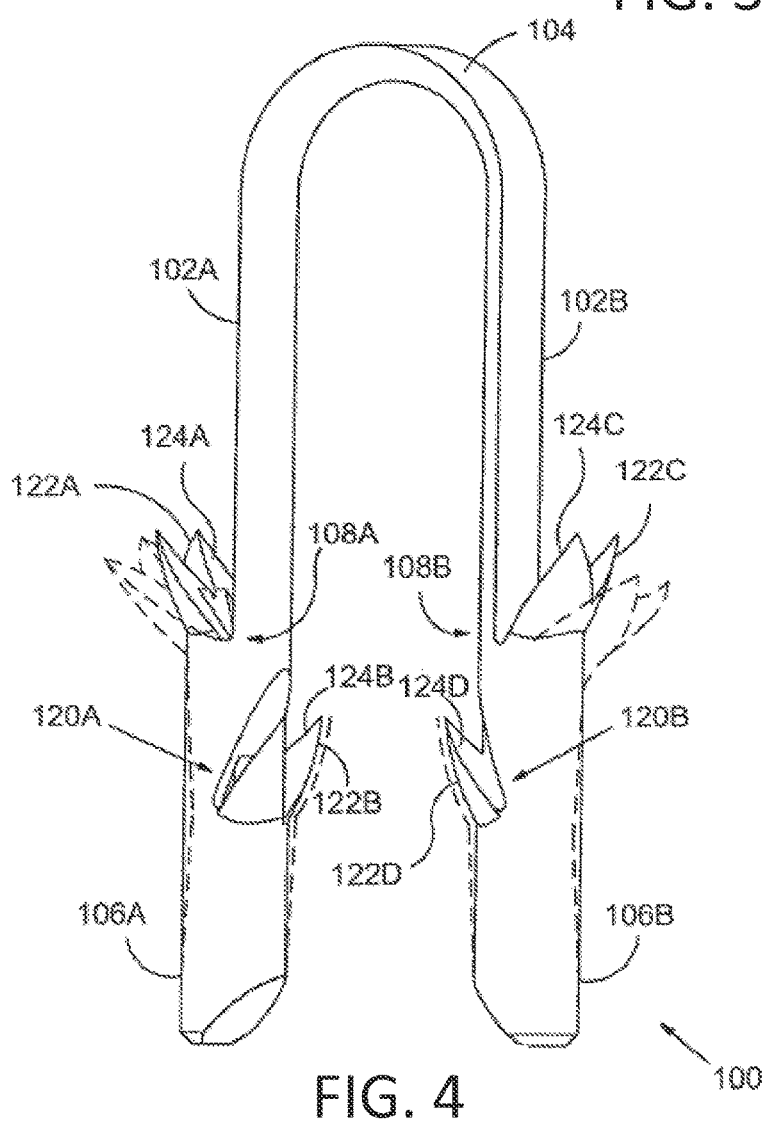
FIG. 4

US 12,414,765 B2

FASTENER DELIVERY SYSTEM AND RELATED METHODS

CROSS REFERENCE TO RELATED APPLICATIONS

This application is a continuation of U.S. patent application Ser. No. 16/934,977 filed Jul. 21, 2020, which is a continuation of U.S. patent application Ser. No. 15/394,350 filed Dec. 29, 2016, which claims the benefit of U.S. Provisional Patent Application Ser. No. 62/273,890 filed on Dec. 31, 2015, the disclosures of which are incorporated herein by reference. This application is also related to U.S. patent application Ser. No. 14/931,423 filed on Nov. 3, 2015, the disclosure of which is incorporated herein by reference.

TECHNICAL FIELD

The present disclosure pertains generally, but not by way of limitation, to medical devices, and methods for using medical devices. More particularly, the present disclosure pertains to devices for introducing and positioning implants within patients, and methods for using such devices.

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. Adequate procedures do not exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. There is an ongoing need to deliver and adequately position medical implants during an arthroscopic procedure in order to treat injuries to the rotator cuff, rotator cuff tendons, or other soft tissue or tendon injuries throughout a body.

SUMMARY OF THE DISCLOSURE

The disclosure describes various medical devices and methods for using medical devices to assist in delivering and positioning implants within a body. An example fastener delivery tool comprises a sheath assembly including a sheath and a position retention member and a retraction assembly including a cover and a retractor member. The cover includes a lumen extending therein. The fastener delivery tool also includes and a handle assembly coupled to a proximal end of the sheath assembly, the handle assembly including a housing and an actuation member. Further, the sheath assembly extends through the lumen of the cover and the retractor member is configured to move relative to the handle between a first position in which the sheath assembly is disposed within a distal portion of the cover and a second position in which the sheath assembly extends out of the distal portion of the cover. Additionally, actuation of the actuation member moves the retractor member from the first position to the second position.

Alternatively or additionally, in another example, wherein the retraction assembly is biased to be in the second position.

Alternatively or additionally, in another example, further comprising a spring coupled to the retractor member.

Alternatively or additionally, in another example, wherein the spring shifts the retractor member from the first position to the second position when the actuation member is actuated.

Alternatively or additionally, in another example, wherein the cover includes one or more leaflets positioned on a distal portion thereof.

Alternatively or additionally, in another example, wherein at least one of the one or more leaflets includes a proximal portion and a distal portion, and wherein at least one of the one or more leaflets are tapered from the proximal portion to the distal portion.

Alternatively or additionally, in another example, wherein the leaflets are biased in a closed position.

Alternatively or additionally, in another example, wherein the leaflets are configured to expand radially outward as the sheath assembly slides from the first position to the second position.

Alternatively or additionally, in another example, wherein shifting the retractor member between the first position and the second position uncovers the sheath assembly in vivo.

Alternatively or additionally, in another example, wherein a proximal portion of the cover is attached to the retractor member.

Alternatively or additionally, in another example, wherein the cover is coaxial with the sheath assembly.

Alternatively or additionally, in another example, wherein the actuation member includes a projection configured to engage with a recess disposed along the retractor member.

Alternatively or additionally, in another example, wherein the actuation member is designed to rotate relative to the housing.

Alternatively or additionally, in another example, wherein actuation of the actuation member rotates the actuation member about an attachment point disposed along the housing, and wherein rotation of the actuation member about the attachment point is designed to disengage the projection from the recess.

Alternatively or additionally, in another example, wherein a longitudinal axis of the handle housing is aligned with a longitudinal axis of the sheath, and wherein the retractor member shifts along both the longitudinal axis of the sheath and the longitudinal axis of the housing.

Another example fastener delivery tool comprises a handle assembly including a housing, a retractor member and an actuation member; and a sheath assembly including a sheath, a cover and a position retention member. Additionally, the sheath extends within a lumen of the cover, a proximal portion of the sheath assembly is coupled to the handle assembly, the retractor member is configured to slide along the handle between a first position in which the sheath assembly is disposed within a distal portion of the cover and a second position in which the sheath assembly extends out of the distal portion of the cover and actuation of the actuation member slides the retractor member from the first position to the second position.

Alternatively or additionally, in another example, wherein the cover includes one or more leaflets positioned on a distal portion thereof.

Alternatively or additionally, in another example, wherein the retractor member is biased to be in the second position.

Alternatively or additionally, in another example, wherein shifting the retractor member between the first position and the second position extends the sheath out of the distal portion of the cover in vivo.

An example method for deploying a fastener comprises positioning a fastener delivery tool adjacent a target site. The fastener delivery tool comprises a sheath assembly including a sheath and a position retention member; a retraction assembly including a cover and a retractor member, wherein the cover includes a lumen extending therein; and a handle assembly coupled to a proximal end of the sheath assembly, the handle assembly including a housing, a trigger and an actuation member. Further, the sheath assembly extends through the lumen of the cover and the retractor member is configured to move along the handle between a first position in which the sheath assembly is disposed within a distal portion of the cover and a second position in which the sheath assembly extends out of the distal portion of the cover. Additionally, actuation of the actuation member moves the retractor member from the first position to the second position. The method also includes deploying a staple along a target site.

The above summary of some examples is not intended to describe each disclosed example device, component, or method or every implementation of the present disclosure. The Brief Description of the Drawings, and Detailed Description, which follow, more particularly exemplify these examples, but are also intended as exemplary and not limiting.

BRIEF DESCRIPTION OF THE DRAWINGS

FIG. 2 is a an alternative perspective view of the tissue fastener or staple of FIG. 1 illustrating other features in accordance with the present disclosure;

FIG. 3 is a top plan view of the tissue fastener or staple of FIG. 1 illustrating the laterally extending legs having lumens for receiving the stakes of a delivery device of the present disclosure;

FIG. 4 is a front plan view of the tissue fastener or staple of FIG. 1 illustrating in phantom flexing of the barbs and legs of the staple in response to grasping of tissue in one example of the present disclosure;

DETAILED DESCRIPTION

Figure 1:
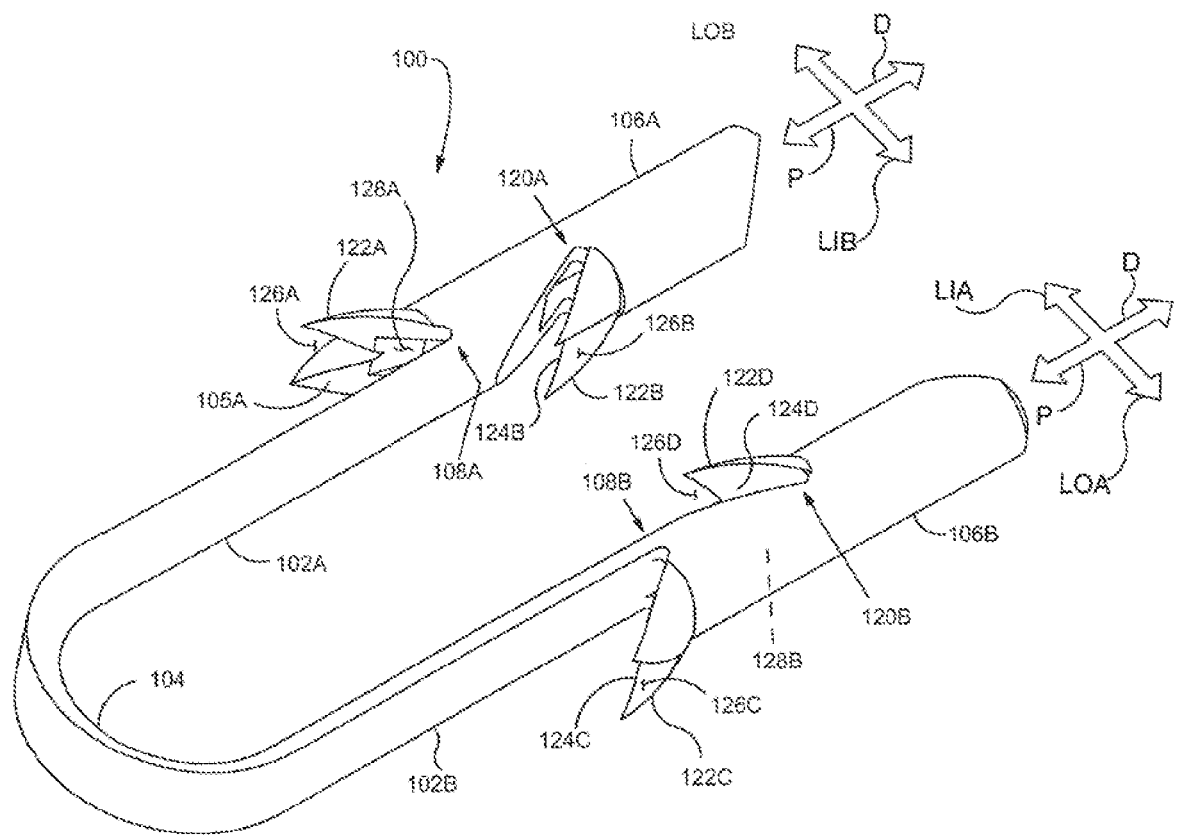
FIG. 1 is a perspective view illustrating an exemplary tissue fastener or staple in accordance with the present disclosure.

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate examples of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", "an example", "some examples", "other examples", etc., indicate that the embodiment(s) and/or example(s) described may include a particular feature, structure, or characteristic, but every embodiment may not necessarily include the particular feature, structure, or characteristic. Moreover, such phrases are not necessarily referring to the same embodiment and/or example. Further, when a particular feature, structure, or characteristic is described in connection with an embodiment and/or example, it would be within the knowledge of one skilled in the art to affect such feature, structure, or characteristic in connection with other embodiments and/or examples, whether or not explicitly described, unless clearly stated to the contrary. That is, the various individual features described below, even if not explicitly shown in a particular combination, are nevertheless contemplated as being combinable or able to be arranged with each other to form other additional embodiments and/or examples or to complement and/or enrich the described embodiment(s) and/or example(s), as would be understood by one of ordinary skill in the art.

FIG. 1 is a perspective view illustrating an exemplary staple 100 in accordance with the present disclosure. Although the various parts of exemplary staple 100 are depicted in relative proportion to other parts of staple 100, other configurations in size and orientation of the various parts are also contemplated in other examples. A number of reference directions are illustrated using arrows in FIG. 1 to assist in understanding the details of staple 100. The illustrated directions include: proximal direction P, distal direction D, first laterally outward direction LOA, second laterally outward direction LOB, first laterally inward direction LIA, and second laterally inward direction LIB.

In some examples, staple 100 comprises first arm 102A, second arm 102B, and bridge 104. Bridge 104 may abut, or extend from or adjacent to, the proximal end of first arm 102A to the proximal end of second arm 102B. First arm 102A may include first trunk 106A, with first trunk 106A generally having a greater width than the rest of first arm 102A as depicted in FIG. 1. In some examples, first arm 102A may also include non-trunk portion 105A. The length of first trunk 106A relative to the overall length of first arm 102A can vary in different examples. For instance, first trunk 106A can extend for the entire length of first arm 102A such that bridge 104 abuts with or is adjacent to first trunk 106A. In other examples, first arm 102A may not include first trunk 106A. That is, first arm 102A may not have a portion with a greater width than the rest of first arm 102A. In such examples, first arm 102A may still have non-trunk portion 105A.

Similarly, second arm 102B may include second trunk 106B, with second trunk 106B generally having a greater width than the rest of second arm 102B. Additionally, second trunk 106B may extend for at least a portion of second arm 102B. A distal portion of second arm 102B may abut the proximal end of second trunk 106B and second arm 102B may further include non-trunk portion 105B. As with first trunk 106A, second trunk 106B may extend along second arm 102B for varying lengths. Additionally, in some examples, second arm 102B may not have a portion with a greater width than the rest of second arm 102B. In FIG. 1, first trunk 106A and second trunk 106B are shown extending distally from a proximal portion of first arm 102A and second arm 102B, respectively.

In the example of FIG. 1, first trunk 106A has a lateral extent, or cross sectional area, that is larger than a lateral extent of the non-trunk portion 105A of first arm 102A and bridge 104. Staple 100 may include a first change in lateral stiffness 108A disposed where the distal end of non-trunk portion 105A of first arm 102A abuts first trunk 106A. As depicted, the change in stiffness is abrupt, but can be gradual in alternative examplessuch as through a gradual change in lateral extent between first trunk 106A and non-trunk portion 105A. In an example where first trunk 106A extends for the full length of the first arm 102A, the change in stiffness may occur where first trunk 106A abuts bridge 104. With reference to the example of FIG. 1, it will be appreciated that first trunk 106A is mounted eccentrically to first arm 102A and second trunk 106B is mounted eccentrically to second arm 102B. As with first trunk 106A, second trunk 106B has a lateral extent, or cross sectional area that is larger than a lateral extent of second arm 102B or bridge 104. Staple 100 may include a second change in lateral stiffness 108B where the distal end of second arm 102B abuts second trunk 106A. Similarly to first arm 102A, in some examples the change in stiffness may be abrupt or gradual. If second trunk 106B extends for the entire length of second arm 102B, the change in stiffness may occur at the abutment with bridge 104. In additional examples where there may be no change in lateral extent between first and second trunks 106A, 106B and first and second arms 102A, 102B, a change in stiffness may be accomplished by the use of different materials for first and second trunks 106A, 106B and first and second arms 102A, 102B.

Some examples of staple 100 may include at least a first projection 122A, 122C and a second projection 122B, 122D, on each of first trunk 106A and second trunk 106B, respectively. First projection 122A, 122C on each trunk 106A, 106B may further include first proximal surface 124A, 124C extending away from each trunk in a first direction, such as out and away from each opposite trunk 106A, 106B. The first direction may be a direction such that first proximal surface 124A, 124C will engage with tissue or bone after the trunk is inserted therein and by natural movement of the tissue or bone. In some examples, a pullout force may be applied to bridge 104 to further engage first proximal surface 124A, 124C with bone or tissue. The natural movement of the bone or tissue or the pullout force creates a first moment centered on the area of reduced stiffness adjacent each trunk, tending to rotate each trunk thereabout. The rotation of each trunk may further provide a greater holding force of staple 100 in bone or tissue. Second projection 122B, 122D may include second proximal surface 124B, 124D extending away from each trunk in a second direction, different from the first direction, such as inward, toward the opposite trunk. For example, the second direction may be selected such that second proximal surfaces 124B, 124D will engage tissue or bone after each trunk is inserted therein and by natural movement of the tissue or bone. In some examples, a pullout force may be applied to bridge 104. A slit or area of reduced cross section in the trunk adjacent the second projections provide an area of weakness so that a second moment is applied to the trunk in response to natural movement of the tissue or bone and/or to a pullout force on bridge 104. This moment causes rotation of the trunk about the area of weakness and increases the holding force of staple 100.

As illustrated in the example of staple 100 in FIG. 1, first trunk 106A includes a first projection 122A disposed at an outer side of trunk 106A and a second projection 122B disposed at an inner side of the trunk. First projection 122A includes a first proximal surface 124A extending away from first trunk 106A in a first direction. With reference to FIG. 1, it will be appreciated that the first direction has an outward lateral component and a proximal component so that first proximal surface 124A extends outwardly and proximally away from first trunk 106A. For example, the first direction may be selected such that first proximal surface 124A will engage tissue or bone proximate the outer side of first trunk 106A after being inserted therein so that a first moment is applied to the trunk in response to natural movement of the tissue or bone and/or to a pullout force on bridge 104. The moment centers on the arm portion of lesser stiffness adjacent the first projection.

In the example of FIG. 1, first trunk 106A includes a first localized area of weakness 120A disposed proximate second projection 122B. Second projection 122B includes a second proximal surface 124B extending away from first trunk 106A in a second direction. The second direction is selected such that second proximal surface 124A will engage tissue or bone proximate the inner side of first trunk 106A when inserted therein so that a second moment is applied to the trunk in response to natural movement of the tissue or bone and/or a pullout force on bridge 104. The moment centers around the area of weakness 120A. The second moment has a direction that is generally opposite a direction of the first moment. It will be appreciated that the second direction has an inward lateral component and a proximal component so that second proximal surface 124B extends inwardly and proximally away from first trunk 106A. In other examples, first arm 102A may not include second projection 122B. In such examples, only a first moment may be applied to first trunk 106A in response to natural movement of the tissue or bone and/or a pullout force on bridge 104.

Second trunk 106B includes a third projection 122C disposed at an outer side of second trunk 106B and a fourth projection 122D disposed at an inner side of the trunk. In the example of FIG. 1, third projection 122C includes a third proximal surface 124C extending away from second trunk 106B in a third direction. With reference to FIG. 1, it will be appreciated that the third direction has an outward lateral component and a proximal component so that third proximal surface 124C extends outwardly and proximally away from second trunk 106B. The third direction is selected such that third proximal surface 124C will engage tissue or bone proximate the outer side of second trunk 106B when inserted therein so that a third moment is applied to the trunk in response to natural movement of the tissue or bone and/or a pullout force on bridge 104.

In the example of FIG. 1, second trunk 106B includes a second localized area of weakness 120B disposed proximate fourth projection 122D. Fourth projection 122D includes a fourth proximal surface 124D extending away from second trunk 106B in a fourth direction. In the example of FIG. 1, the fourth direction is selected such that second proximal surface 124A will engage tissue or bone proximate the inner side of second trunk 106B when inserted therein so that a fourth moment is applied to the trunk in response to natural movement of the tissue or bone and/or a pullout force on bridge 104. The fourth moment has a direction that is generally opposite a direction of the third moment. It will be appreciated that the fourth direction has an inward lateral component and a proximal component so that fourth proximal surface 124D extends inwardly and proximally away from second trunk 106B. In other examples, second arm 102B may not include second projection 122D. In such examples, only a first moment may be applied to second trunk 106B in in response to natural movement of the tissue or bone and/or a pullout force on bridge 104.

As depicted in FIG. 1, the staple 100 includes proximal projections that extend away from or outward from the bridge 104, while the distal projections extend inward or toward the center of the bridge 104. This creates generally opposing forces in response to tension on the bridge which, in combination with areas of weakness or reduced lateral extent, substantially increases the holding force of the staple in bone as the different portions of the trunks tend to rotate in opposite directions and apply force to an opposing wall in the hole in bone in which the staple is positioned. It is however, understood that other configurations of the projections are possible. In some examples, only two projections are included and they extend in different directions to cause different force responses as tension is applied to the bridge. Additional examples may include varying numbers of projections which produce one or more moments in each of arms 102A, 102B.

In some examples, each projection of staple 100 may be clefted to form a plurality of points for greater retention in tissue. In the example of FIG. 1, first projection 122A of first trunk 106A defines a first notch 126A that divides first projection 122A into a first sub-projection and a second sub-projection. Second projection 122B of second trunk 106B defines a second notch 126B. In the example of FIG. 1, second notch 126B divides second projection 122B into a first sub-projection and a second sub-projection. Third projection 122C of second trunk 106B defines a third notch 126C that divides third projection 122C into a first sub-projection and a second sub-projection. Fourth projection 122D of second trunk 106B defines a fourth notch 126D that divides fourth projection 122D into a first sub-projection and a second sub-projection.

With continued reference to FIG. 1 and further reference to FIGS. 2 and 3, first trunk 106A defines a first cavity 128A and second trunk 106B defines a second cavity 128B. In the examples of FIGS. 1, 2 and 3, first cavity 128A extends into first trunk 106A and second cavity 128B extends into second trunk 106B. The cavity is sized to cooperate with a staple delivery device for holding and inserting the staple into tissue or bone, as later described in detail herein. In summary, the staple delivery device includes longitudinally extending stakes that fit within the cavities 128A, 128B to hold the staple 100 and push it into position in the tissue as the stake abuts a portion of its respective trunk. In some examples the cavity may extend through a portion of the length of each trunk, as best depicted in FIG. 2 which indicates the distal end of the staple 100 is closed. Alternatively, first cavity 128A and second cavity 128B may extend through the entire length of each trunk 106A, 106B or other portions of staple 100 in some examples. As illustrated by the top view of the staple 100 in FIG. 3, first cavity 128A and second cavity 128B each have a generally rectangular or square cross-sectional shape to cooperate with a similarly shaped cross section on a staple delivery device. However, that first cavity 128A and second cavity 128B may have various cross-sectional shapes to cooperate with alternative staple delivery device designs without deviating from the spirit and scope of the present disclosure.

FIG. 4 is an alternative perspective view of example staple 100 depicted in FIG. 1. In particular, FIG. 4 illustrates in phantom the flexing and bending of the trunks 106A and 106B after implant in response to natural movement of the tissue or bone and/or to tension applied to the bridge.

The combination of projections, areas of weakness and changes in lateral extent described with respect to FIGS. 1, 2, and 3 provide desired flexing, bending and rotating of the trunk in response to natural movement of the tissue or bone and/or to pull out forces on bridge 104. Together the various components of staple 100 act as tissue retention members. An exemplary deflected shape is shown with dashed lines in FIG. 4. Forces applied to staple 100 in response to natural movement of the tissue or bone and/or pullout forces applied to bridge 104 may urge staple 100 to assume the deflected shape shown in FIG. 4. In some additional examples, distally directed forces may be applied on staple 100 using, for example, the staple delivery system shown later and described herein. In some applications, the staple delivery tool may be used to urge first projection 122A and third projection 122C into orientations which lock staple 100 into a target tissue. For example, first projection 122A and third projection 122C may be rotated so that these projections engage the target tissue. When this is the case, tension extending through bridge 104 of staple 100 may keep first projection 122A and third projection 122C in the rotated position. Also when this is the case, the projections may inhibit staple pullout. Further, rotation of any projection causes a rotational force and imparts, within limits defined by the hole in the bone, some rotation to an adjacent portion of the trunk which contacts or engages the wall of the hole in the bone. Increased pullout forces, such as by natural movement of the tissue or bone and/or pullout forces applied to bridge 104, may result in increasing holding force with this design.

Figure 5:
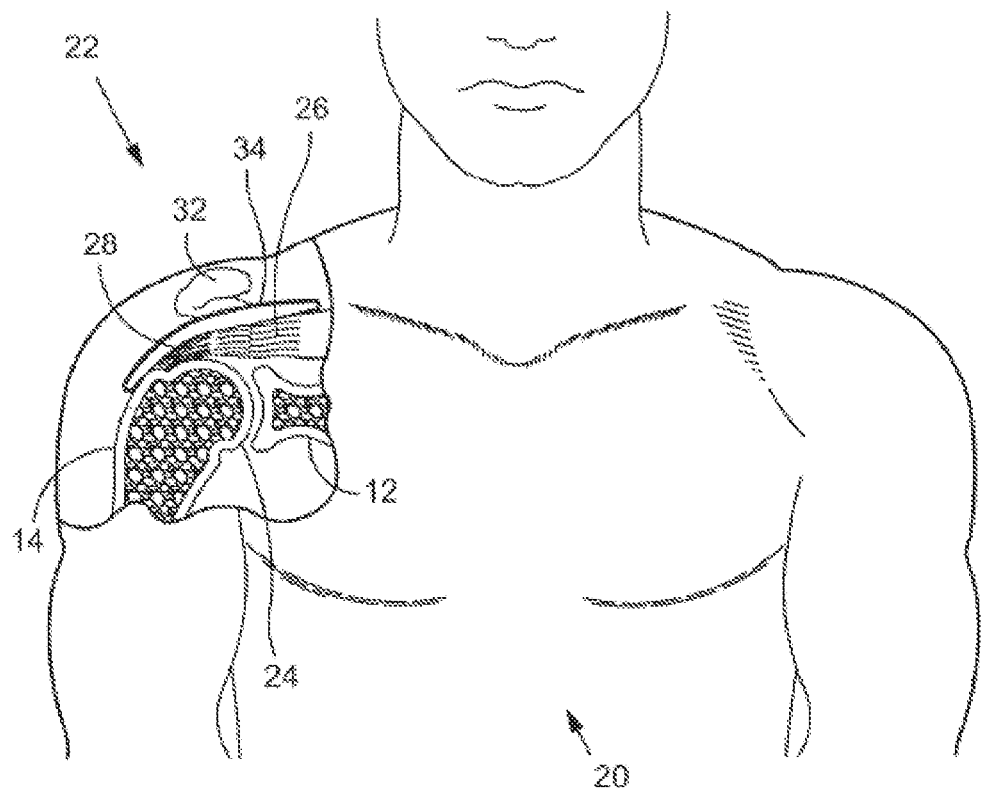
FIG. 5 is a stylized anterior view of a shoulder including a humerus and a scapula.

Next referring to FIG. 5, an exemplary use or application of the staples of the present disclosure is described. FIG. 5 is a stylized anterior view of a patient 20. For purposes of illustration, a shoulder 22 of patient 20 is shown in cross-section in FIG. 5. Shoulder 22 includes a humerus 14 and a scapula 12. In FIG. 5, a head 24 of humerus 14 can be seen mating with a glenoid fossa of scapula 12 at a glenohumeral joint. With reference to FIG. 5, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 5.

With reference to FIG. 5, a distal tendon 28 of the supraspinatus 26 meets humerus 14 at an insertion point. Scapula 12 of shoulder 22 includes an acromium 32. In FIG. 5, a subacromial bursa 34 is shown extending between acromium 32 of scapula 12 and head 24 of humerus 14. Subacromial bursa 34 is shown overlaying supraspinatus 26 as well as supraspinatus tendon 28 and a portion of humerus 14. Subacromial bursa 34 is one of the hundreds of bursae found the human body. Each bursa comprises a fluid filled sac. The presence of these bursae in the body reduces friction between bodily tissues.

The exemplary staples or fasteners described herein may be used to affix tendon repair implants to various target tissues. The shoulder depicted in FIG. 5 is one example where a tendon repair implant may be affixed to one or more bones associated with an articulating joint, such as the glenohumeral joint. Additionally, the tendon repair implant may be affixed to one or more tendons to be treated. The tendons to be treated may be torn, partially torn, have internal micro-tears, be untorn, and/or be thinned due to age, injury or overuse. The methods and apparatus of the present disclosure and related devices may provide beneficial therapeutic effect on a patient experiencing joint pain believed to be caused by partial thickness tears and/or internal micro-tears. By applying a tendon-repair implant early before a full tear or other injury develops, the implant may cause the tendon to thicken and/or at least partially repair itself, thereby avoiding more extensive joint damage, pain, and the need for more extensive joint repair surgery.

Figure 6:
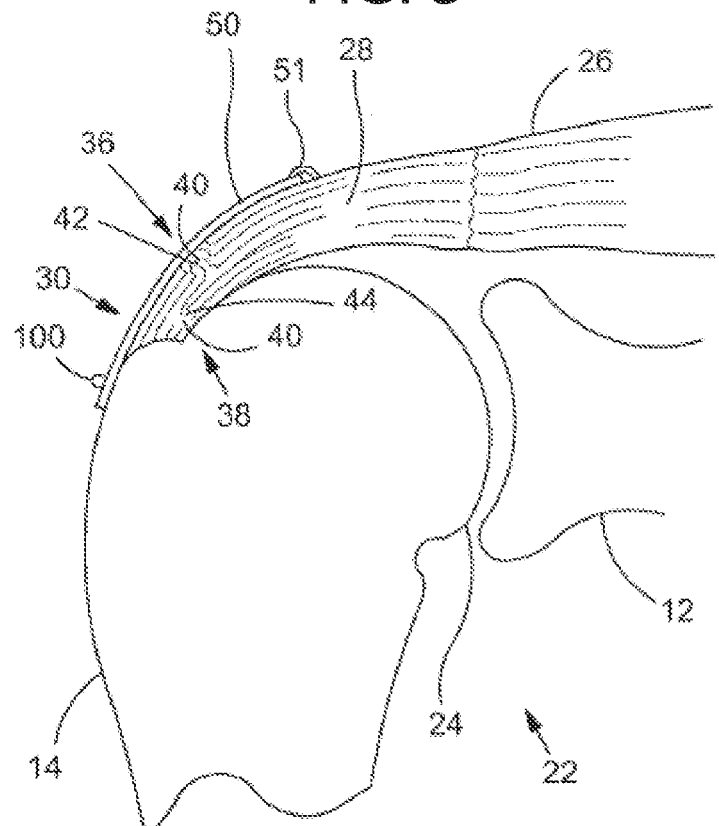
FIG. 6 is a stylized anterior view of a shoulder depicting the head of the humerus shown mating with the glenoid fossa of the scapula at a glenohumeral joint and a sheet-like material is affixed to the tendon.

FIG. 6 is a stylized anterior view of a shoulder 22 including a humerus 14 and a scapula 12. In FIG. 6, a head 24 of humerus 14 is shown mating with a glenoid fossa of scapula 12 at a glenohumeral joint. A supraspinatus 26 is also shown in FIG. 6. This muscle, along with others, controls the movement of humerus 14 relative to scapula 12. A distal tendon 28 of supraspinatus 26 meets humerus 14 at an insertion point 30.

As depicted in FIG. 6, distal tendon 28 includes a first damaged portion 36. A number of loose tendon fibers 40 in first damaged portion 36 are visible in FIG. 6. First damaged portion 36 includes a first tear 42 extending partially through distal tendon 28. First tear 42 may therefore be referred to as a partial thickness tear. With reference to FIG. 6, first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 6, distal tendon 28 includes a second damaged portion 38 located near insertion point 30. As illustrated, second damaged portion 38 of distal tendon 28 has become frayed and a number of loose tendon fibers 40 are visible. Second damaged portion 38 of distal tendon 28 includes second tear 44. Second tear 44 begins on the side of distal tendon 28 facing the center of the humeral head 24. Accordingly, second damaged portion 38 may be referred to as an articular side tear.

FIG. 6 illustrates sheet-like implant 50 has been placed over the bursal side of distal tendon 28. Sheet-like implant 50 is affixed to distal tendon 28 by a plurality of tendon staples 51. Sheet-like implant 50 is affixed to humerus 14 by one or more bone staples 100 in accordance with designs of staples disclosed herein. Sheet-like implant 50 extends over insertion point 30, first tear 42 and second tear 44. Some methods in accordance with this disclosure may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon.

Figure 7:
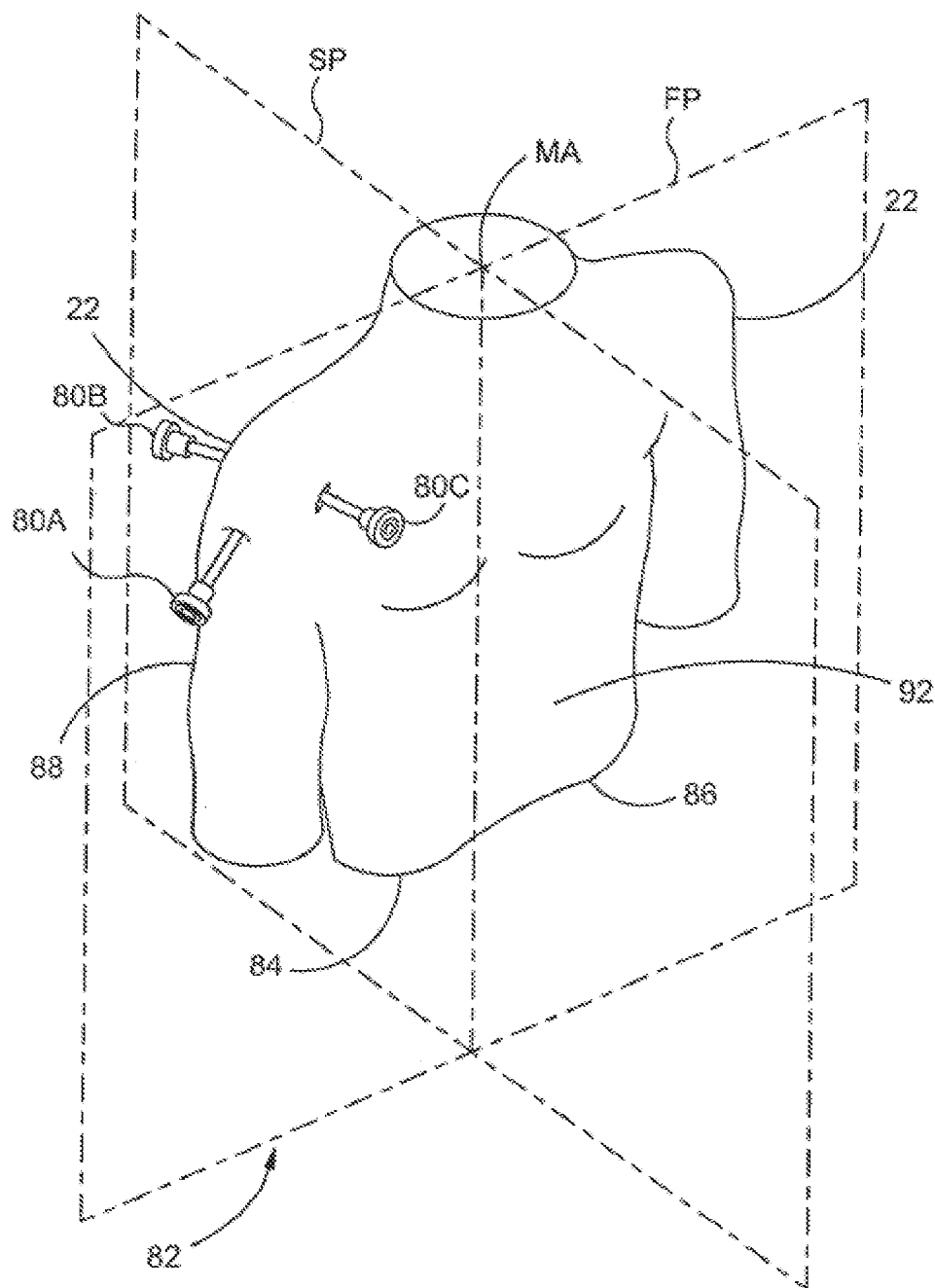
FIG. 7 is a stylized perspective view showing a portion of the body of a human patient divided into quadrants by planes for descriptive purposes herein.

FIG. 7 is a stylized perspective view showing a portion of the body 82 of a human patient 20. Body 82 includes a shoulder 22. In the example of FIG. 7, a plurality of cannulas are positioned to access a treatment site within shoulder 22.

In some cases, shoulder 22 may be inflated by pumping a continuous flow of saline through shoulder 22 to create a cavity proximate the treatment site. The cannulas shown in FIG. 7 include a first cannula 80A, a second cannula 80B and a third cannula 80C.

In FIG. 7, a sagital plane SP and a frontal plane FP are shown intersecting body 82. Sagital plane SP and frontal plane FP intersect one another at a medial axis MA of body 82.

With reference to FIG. 7, sagital plane SP bisects body 82 into a right side 84 and a left side 86. Also with reference to FIG. 7, frontal plane FP divides body 82 into an anterior portion 92 and a posterior portion 88. Sagital plane SP and a frontal plane FP are generally perpendicular to one another. These planes and portions are used to describe the procedures used in various examples.

First cannula 80A is accessing a treatment site within shoulder 22 using a lateral approach in which first cannula 80A pierces the outer surface of right side 84 of body 82. The term lateral approach could also be used to describe situations in which an instrument pierces the outer surface of left side 86 of body 82. Second cannula 80B is accessing a treatment site within shoulder 22 using a posterior approach in which second cannula 80B pierces the outer surface of posterior portion 88 of body 82. Third cannula 80C is accessing a treatment site within shoulder 22 using an anterior approach in which third cannula 80C pierces the outer surface of anterior portion 92 of body 82.

Figure 8:
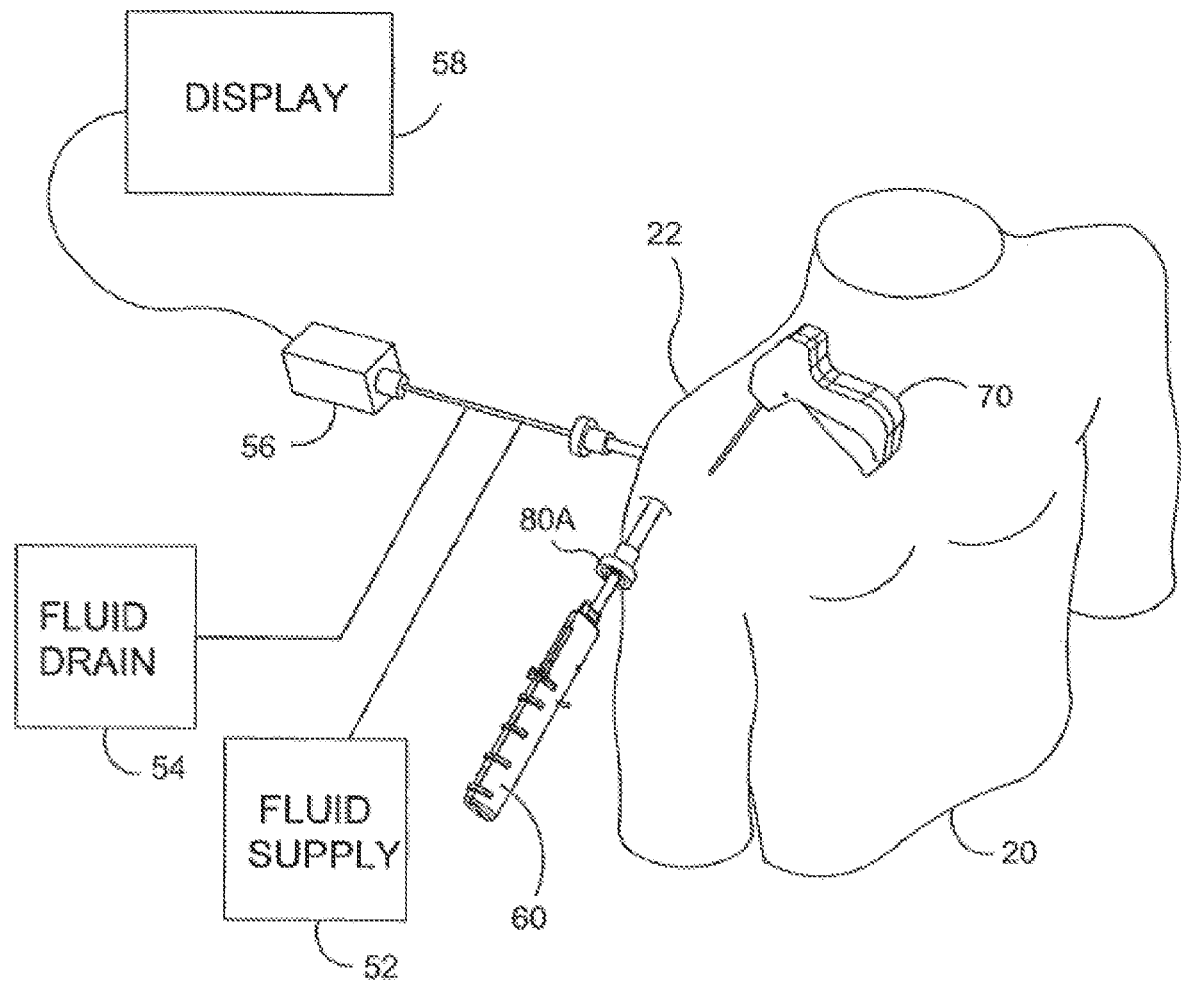
FIG. 8 is a stylized perspective view illustrating an exemplary procedure for arthroscopic treatment of a shoulder of a patient in accordance with one example of the present disclosure.

FIG. 8 is a stylized perspective view illustrating an exemplary procedure for treating a shoulder 22 of a patient 20. The procedure illustrated in FIG. 8 may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 8 has been inflated to create a cavity therein. A fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be affixed to a bursal surface of the tendon regardless of whether there are visible signs of tendon damage.

An implant delivery system 60 can be seen extending from shoulder 22 in FIG. 8. Implant delivery system 60 is extending through a first cannula 80A. In certain examples, first cannula 80A can access a treatment site within shoulder 22 using a lateral approach in which first cannula 80A pierces the outer surface of a right side of the patient's body. In some cases a physician may choose not to use a cannula in conjunction with implant delivery system 60. In such examples, the implant delivery system may be advanced through tissue. Implant delivery system 60 comprises a sheath that is affixed to a handle. The sheath defines a lumen and a distal opening fluidly communicating with the lumen. In the example of FIG. 8, the distal opening of the sheath has been placed in fluid communication with the cavity created in shoulder 22.

A tendon repair implant is at least partially disposed in the lumen defined by the sheath of implant delivery system 60. Implant delivery system 60 can be used to place the tendon repair implant inside shoulder 22. In some examples, the tendon repair implant is folded into a compact configuration when inside the lumen of the sheath. When this is the case, implant delivery system 60 may be used to unfold the tendon repair implant into an expanded shape. Additionally, implant delivery system 60 can be used to hold the tendon repair implant against the tendon.

The tendon repair implant may be affixed to the tendon while it is held against the tendon by implant delivery system 60. Various attachment elements may be used to fix the tendon-repair implant to the tendon. Examples of attachment elements that may be suitable in some applications include sutures, tissue anchors, bone anchors, and staples. In the example of FIG. 8, the shaft of a fixation tool 70 is shown extending into shoulder 22. In some examples, fixation tool 70 is capable of fixing the tendon repair implant to the tendon and bone with one or more staples of the present disclosure while the tendon repair implant may be held against the tendon by implant delivery system 60.

Figure 9:
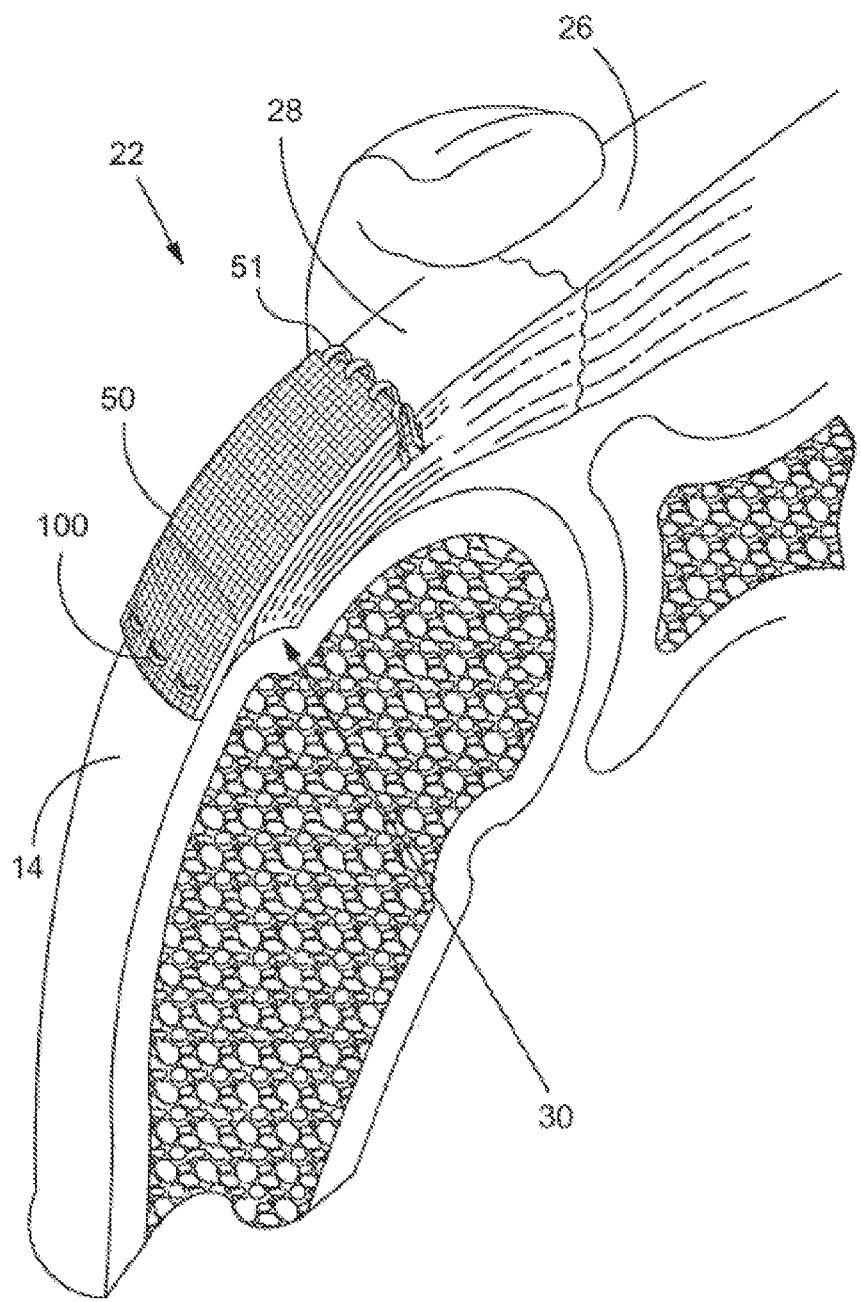
FIG. 9 is a stylized perspective view of a shoulder including a supraspinatus having a distal tendon with a sheet-like material affixed thereto.

FIG. 9 is a stylized perspective view of a shoulder 22 including a supraspinatus 26 having a distal tendon 28. With reference to FIG. 9, a tendon repair implant 50 has been affixed to a surface of distal tendon 28. Tendon repair implant 50 may comprise, for example, various sheet-like structures without deviating from the spirit and scope of the present detailed description. In some examples, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some examples, the sheet-like structure may comprise a laminate including multiple layers of film with each layer of film defining a plurality of micro-machined or formed holes. The sheet-like structure of the tendon repair implant may also comprise a reconstituted collagen material having a porous structure. Additionally, the sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Fremont, California which identifies these materials using the trademark BIOMATERIAL™. The sheet-like structure may be circular, oval, oblong, square, rectangular, or other shape configured to suit the target anatomy.

In the examples of FIG. 9, sheet-like implant 50 is affixed to distal tendon 28 by a plurality of tendon staples 51. Sheet-like implant 50 is affixed to humerus 14 by a plurality of bone staples 100 as described with respect to the exemplary embodiment of FIG. 1 and detailed throughout this disclosure. However, in other examples, as described previously, various attachment elements may be used to fix tendon repair implant 50 to distal tendon 28 without deviating from the spirit and scope of this detailed description. Example attachment elements that may be suitable in some applications include sutures, tissue anchors, bone anchors, and staples.

In some exemplary methods, a plurality of staples may be applied using a fixation tool. After the staples are applied, the fixation tool may be withdrawn from the body of the patient. Distal tendon 28 meets humerus 14 at an insertion point 30. With reference to FIG. 9, it will be appreciated that sheet-like implant 50 extends over insertion point 30. Tendon repair implant may be applied to distal tendon 28, for example, using the procedure illustrated in the previous figures. In various examples, staples may straddle the perimeter edge of the sheet-like implant (as shown in FIG. 9), may be applied adjacent to the perimeter, and/or be applied to a central region of the implant. In some examples, the staples may be used to attach the implant to soft tissue and/or to bone.

Staples or fasteners 100, as exemplified in FIG. 1 and described and illustrated herein can be used to attach tissue and implants to bone. In at least some embodiments, the staple is generally flexible and includes areas of relative lateral weakness on the trunks and can further include an increase in flexibility at the transition from the trunk to the non-trunk portion of the arm or the transition from the trunk to the bridge. As described above, these areas of increased flexibility provide improved staple retention as these portions allow flexing and bending in response to increasing pullout forces. With this flexibility, the fasteners cannot be pounded or driven into bone or other tissue as a conventional hard staple would be driven into paper, wood, tissue or bone. Therefore, for application of the staple of the present disclosure to affix tissue or implants to bone, the staple may be included in a kit that may also include a staple delivery device 200 and various inserts, including pilot hole forming insert assembly 270 as disclosed herein.

Figure 10:
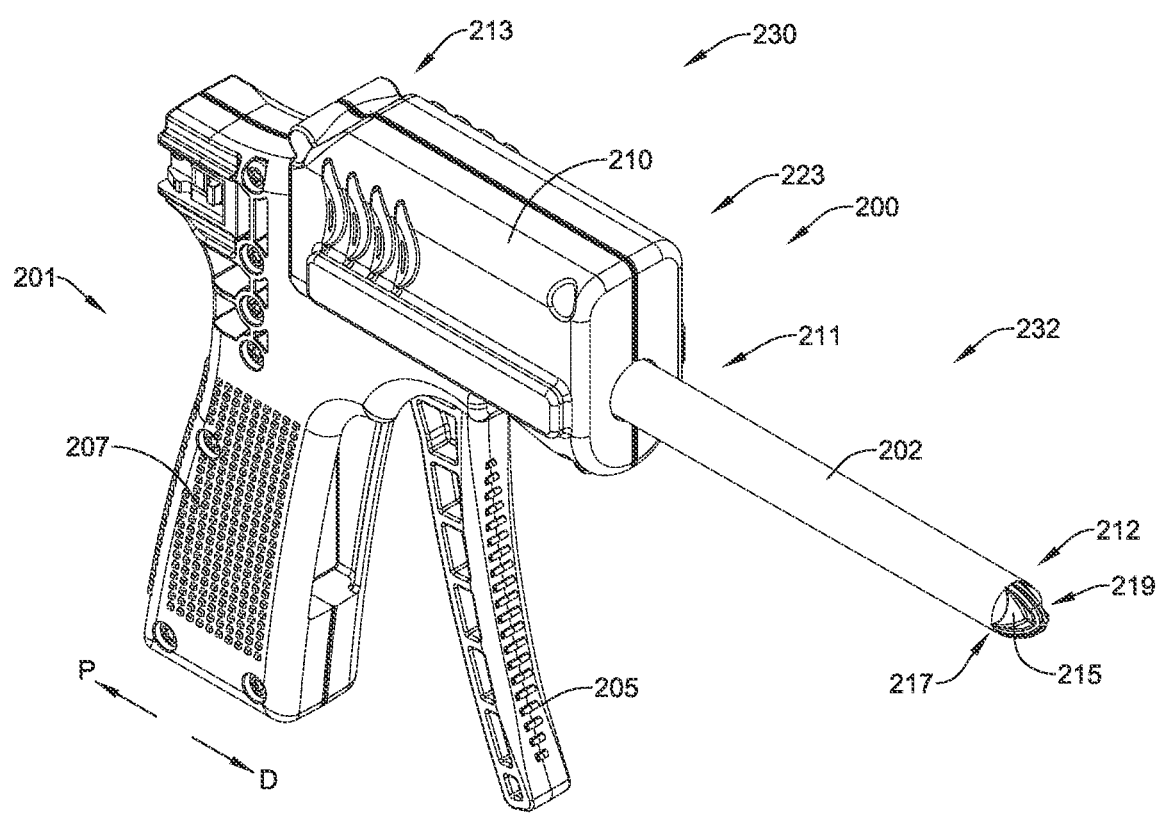
FIG. 10 is a perspective view illustrating an example fastener delivery device in accordance with one example of the present disclosure.

FIG. 10 is a schematic illustration depicting a perspective views of staple delivery device 200. As shown on several figures used herein to describe various features of staple delivery device 200, the proximal direction is represented by arrow "P" and the distal direction is represented by arrow "D." Further, as shown in FIG. 10, staple delivery device 200 may include handle assembly 201, retraction assembly 230 and sheath assembly 232.

Handle assembly 201 may include a housing 207 and trigger handle 205. In some example, trigger handle 205 may be utilized to apply a removal force to one or more inserts utilized by staple delivery device 200. For example, in some examples trigger handle 205 may rotate and/or pivot relative to housing 207 such that a leveraged force is applied to an insert placed within staple delivery device 200. Additional examples of the trigger handle 205 and the removal forces generated therewith are described in U.S. patent application Ser. No. 14/931,423 filed on Nov. 3, 2015, the disclosure of which is incorporated herein by reference.

Figure 11:
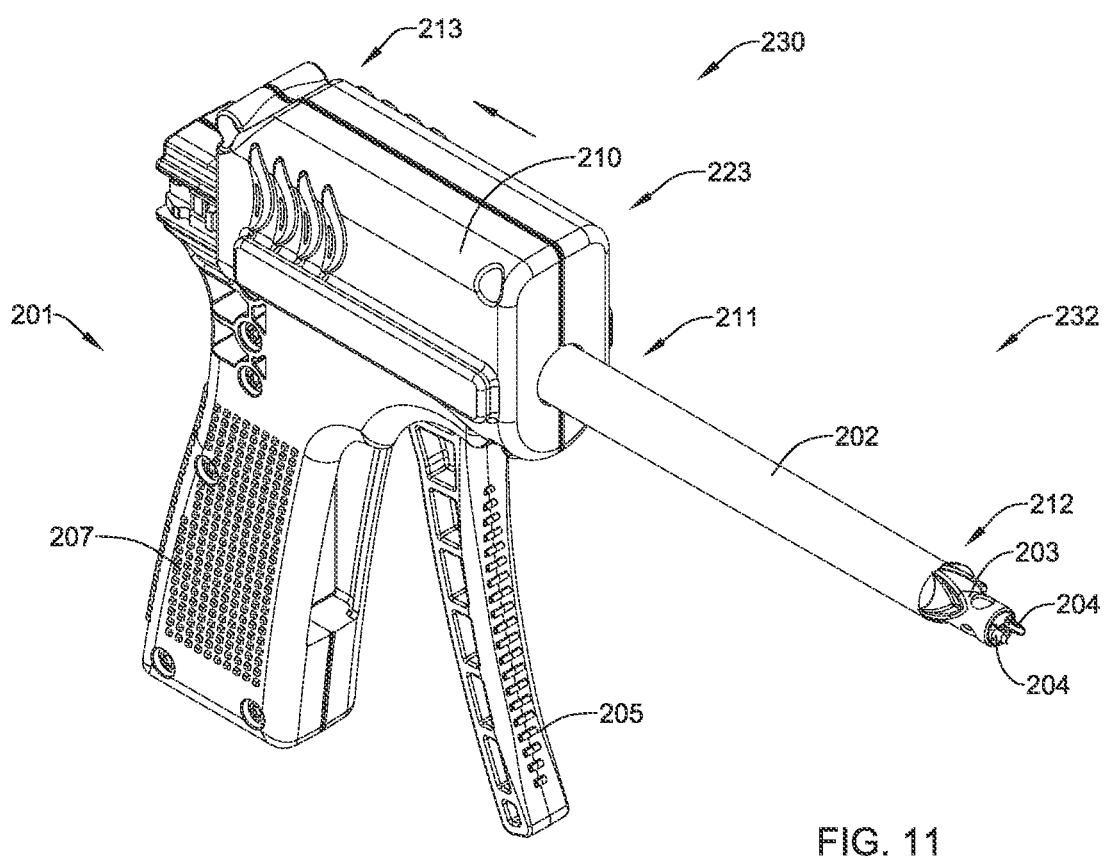
FIG. 11 is a perspective view illustrating an example fastener delivery device in accordance with one example of the present disclosure.

Sheath assembly 232 may include sheath 203 (shown in FIG. 11) and one or more position retention members 204 (shown in FIG. 11). The one or more position retention members 204 may be attached to and extend distally from a distal portion of sheath 203. Sheath member 203 may be a hollow tube and be configured to receive one or more inserts into its lumen. For example, sheath member 203 may be configured to receive a pilot hole insert assembly 270.

A proximal portion of sheath assembly 232 may be attached to handle assembly 201. For example, a proximal portion of sheath assembly 232 may extend into a portion of handle assembly 201 and be rigidly fixed within handle assembly 201. In some examples, a proximal portion of the sheath 232 may engage (e.g., mate) with the interior structural elements of handle assembly 201. For example, handle assembly 201 may include a recess or cavity designed to engage and/or mate with the proximal portion of sheath assembly 232. It can be appreciated that in some examples, sheath assembly 232 is fixed relative to handle assembly 201. In other words, in some examples sheath 232 does not move, slide, translate, etc. with respect to handle assembly 201.

Retraction assembly 230 may include cover 202 and retractor member 210. Cover 202 may include a proximal portion 211 and a distal portion 212. Further, cover 202 may include a lumen extending the length of cover 202. For example, the lumen extending within cover 202 may extend along the longitudinal axis of cover 202 from proximal portion 211 to distal portion 212.

The distal portion 212 of cover 202 may include one or more leaflets 215. For example, the distal portion 212 of cover 202 may include 1, 2, 3, 4, 5, 6, 7, 8, 9, 10 or more leaflets. In some instances (such as that shown in FIG. 10), leaflets 215 may be positioned on the distal end of cover 202.

In some instances, the proximal portion 211 of cover 202 may be attached to a distal portion of retractor member 210. For example, FIG. 10 shows proximal portion 211 of cover 202 extending into distal portion 223 of retractor member 210. In some examples, a proximal portion of the cover 202 may engage (e.g., mate) with the interior structural elements of retractor member 210. For example, retractor member 210 may include a recess or cavity designed to engage and/or mate with the proximal portion of retractor member 210. It can be appreciated that in some examples, cover 202 is fixed relative to retractor member 210. In other words, in some examples cover 202 and retractor member 210 move, slide, and/or translate as a combined assembly. Additionally, in some instances cover 202 may extend over a portion of sheath member 203. In other words, in some examples, sheath 203 may be positioned within the lumen of cover 202.

As illustrated by FIGS. 10 and 11, in some examples retraction assembly 230 may slide, move, translate and/or shift with respect to sheath assembly 232 and handle assembly 201. Specifically, staple delivery device 200 may include a first configuration (e.g., position) in which the cover 202 of retraction assembly 232 encloses (e.g., covers) sheath assembly 232. This configuration may correspond to the retraction assembly 230 being moveable along handle assembly 201 to a distal position along handle assembly 201. Further, staple delivery device 200 may include a second configuration in which the cover 202 of retraction assembly 230 does not completely enclose sheath assembly 232. As shown in FIG. 11, the second configuration may correspond to retraction assembly 230 being moveable proximally along handle assembly 201. In other words, the retraction assembly 230 (e.g., retractor member 210 and cover 202) may slide, move or shift as a single piece along handle assembly 201. Further, when retraction assembly 230 moves from a distal position to a proximal position, the distal portion 212 of cover 202 may be positioned proximal of a distal portion of sheath member 203 (thereby "uncovering" a distal portion of sheath 203).

As shown in FIG. 11, leaflets 215 may hinge, flex, pivot, rotate and/or expand outward in a radial direction, thereby creating an opening through which sheath assembly 232 may extend. For example, as retraction assembly 230 moves from a first, distal position to a second, proximal position, leaflets 215 may flare open (as shown in FIG. 11) as the distal portion 212 of cover 202 moves over the distal portion of the sheath assembly 232.

Additionally, leaflets 215 may include a proximal portion 217 and a distal portion 219. In some examples, one or more of leaflets 215 may taper from proximal portion 217 to distal portion 219. Further, each leaflet 215 may curve inward toward longitudinal axis 221 (shown in FIG. 12) and taper as each leaflet 215 extends distally. In at least some embodiments, cover 202 comprises an even number of leaflets 215. More specifically, in at least some embodiments, cover 202 comprises four, six, eight, ten, or any other suitable number of leaflets 215. However, in other embodiments, cover 202 may comprise an odd number of leaflets 215.

In examples where cover 202 comprises an even number of leaflets 215, as staple delivery system 200 is being inserted into an incision, opposite leaflets 215 may collapse against each other when being advanced through the incision and into tissue. This may help prevent tissue from entering cover 202. For instance, each leaflet 215 may have a thickness extending from an outer surface to an inner surface. The leaflet thickness may vary in different embodiments between about 0.05 inches (1.27 mm) and about 0.15 inches (3.81 mm). As a force is applied to the outer surface of leaflets 215 and leaflets 215 collapse together such that one leaflet 215 converges with an adjacent face of an adjacent leaflet 215, leaflets 215 may become pressed together. In this manner, each of leaflets 215 may support each other when a force is applied to the outer surface of leaflets 215. The thickness and configuration of leaflets 215 may help to prevent leaflets 215 from buckling inward when forces are applied to the outside surface of leaflets 215. With leaflets 215 pressed together (e.g. abutting one another), leaflets 215 may form a solid plug which prevents tissue from entering cover 202 as staple delivery system 200 is advanced through tissue. Additionally, when leaflets 215 are pressed together under an external force, leaflets 215 may translate such forces into a force acting in a substantially axial direction (e.g., along central longitudinal axis 221).

As discussed above, when a force is applied to the outer surface of leaflets 215, leaflets 215 are configured to collapse together. However, when a force is applied to an inner surface of leaflets 215 (e.g., from an interior of the cover 202), the force may push leaflets 215 in an outward direction away from each other. If the force is large enough, leaflets 215 flare radially outward and diverge from one another, exposing sheath assembly 232.

Additionally, while FIGS. 10 and 11 show leaflets 215 including a cavity or recess formed in the sidewall thereof, it is contemplated that leaflets 215 may include a variety of geometric shapes and/or configurations tailored to a specific functionality.

For example, it may be desirable for a clinician to insert staple delivery device 200 through an access site of a patient while cover 202 is positioned over sheath assembly 232. Specifically, cover 202 (including leaflets 215) may allow position retention members 204 to slide past tissue (e.g., access site) without getting caught on skin. In other words, cover 202 may protect, or guard against, position retention members 204 from getting caught on the tissue. For example, the tissue defining the access site may slide around the curved surfaces of cover 202 (including leaflets 215), thereby allowing the clinician to advance staple delivery device 200 through the tissue without any portions of staple delivery device 200 catching on tissue.

The ability of cover 202 to prevent portions of staple delivery device 200 from catching on tissue may be desirable for a variety of reasons. For example, cover 202 may permit a clinician to use the staple delivery device 200 independent of a separate access cannula. As stated above, cover 202 may prevent position retention members 204 from catching on tissue (similar to the functionality provided by a separate access cannula). As the user advances staple delivery device 200 into the patient, the tissue may slide along cover 202 and past position retention members 204. In this manner, a user may maneuver staple delivery device 200 to an implant site without catching position retention members 204 on tissue of the patient causing unwanted tissue damage.

Figure 12:
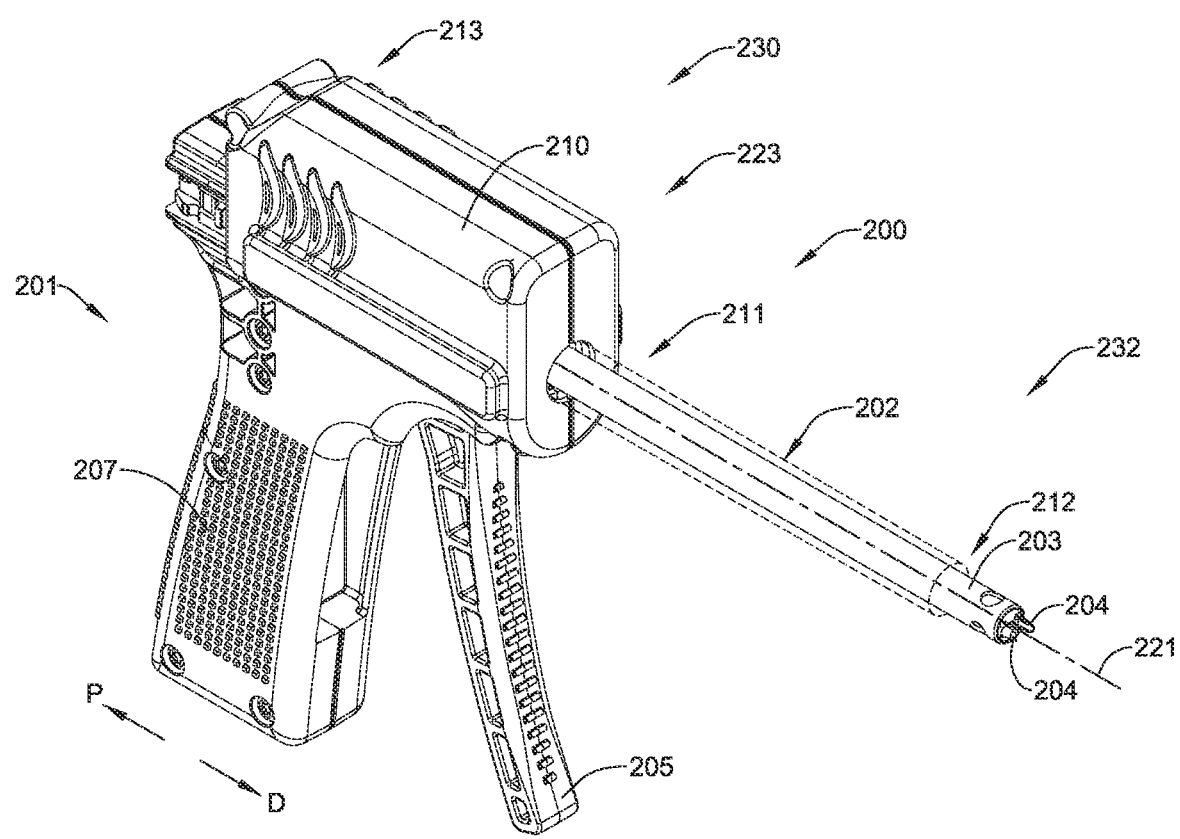
FIG. 12 is a perspective view illustrating an example fastener delivery device in accordance with one example of the present disclosure.
Figure 13:
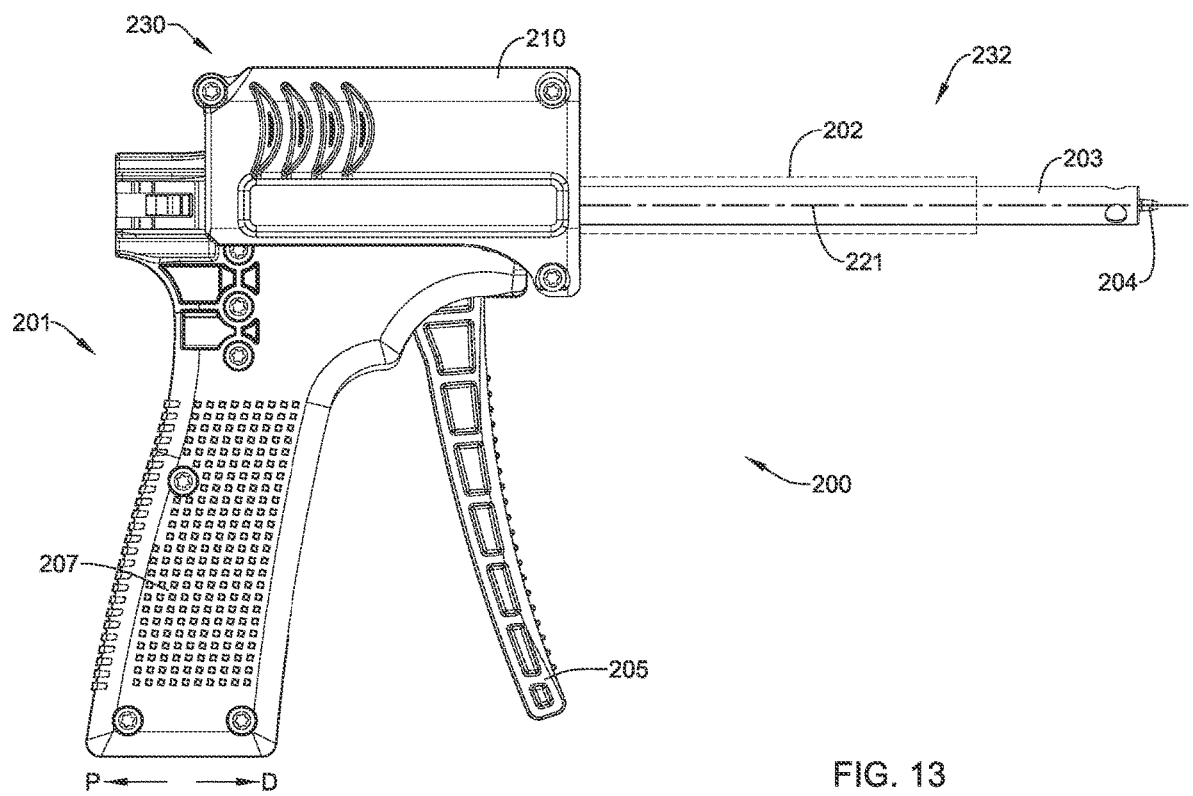
FIG. 13 is a plan view illustrating an example fastener delivery device in accordance with one example of the present disclosure.

FIGS. 12 and 13 illustrate alternative views of staple delivery device 200. Namely, FIGS. 12 and 13 show sheath assembly 232 including sheath 203 and position retention members 204 extending within a portion of cover 202 (depicted by dotted line 213). As shown, sheath assembly 232 includes a longitudinal axis 221. It can be appreciated that cover 202 and sheath member 203 may be coaxial with one another along the longitudinal axis 221. Further, FIG. 213 illustrates that retractor member 210 may move relative to handle assembly 201 along a line which is substantially parallel to or aligned with the longitudinal axis 221. However, this is not intended to be limiting. Other means are contemplated for moving retractor member 210 with respect to handle assembly 201. For example, it can be appreciated that retractor 210 may rotate, pivot, spin and/or swing away from handle assembly 201 and/or sheath assembly 232. These alternative methods may retract the retractor member 210 to achieve substantially the same results (e.g., uncovering the distal portion of the sheath assembly 232) as those discussed above with respect to the linear retraction of the retractor member 210.

It can be appreciated that in order for retractor member 210 (along with cover 202) to move relative to handle assembly 201, one or more forces needs to be imparted to the retractor member 210 such that it moves from a distal position to a proximal position (in which the sheath assembly extends through cover 202 as described above). In some examples, a spring (either in tension or compression) may be utilized to provide the linear force necessary to move the retractor member 210 relative to handle assembly 201.

Figure 14:
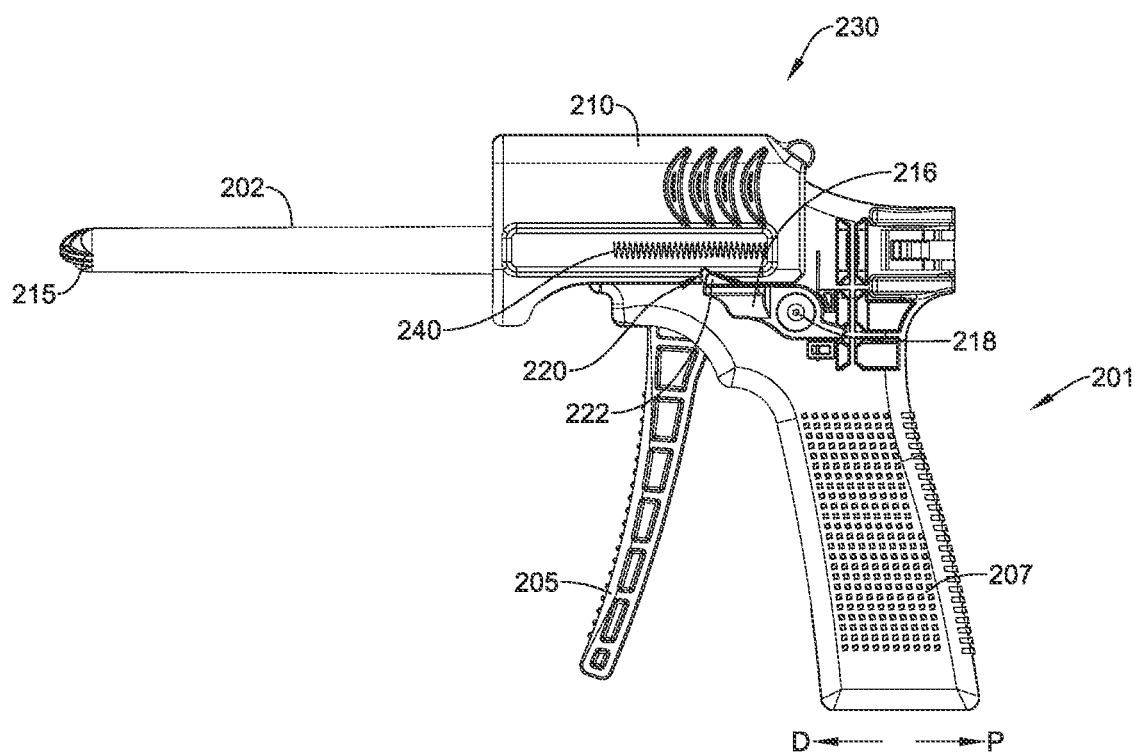
FIG. 14 is a plan view illustrating an example fastener delivery device in accordance with one example of the present disclosure.

FIG. 14 shows staple delivery device 200 including spring 240 positioned within handle assembly 201. While spring 240 is shown in FIG. 14 to be generally in tension, it is contemplated that alternative embodiments could incorporate spring 240 in compression.

It can be appreciated from FIG. 14 that spring 240 may bias retractor member 210 in a proximal position. In other words, spring 240 may "pull" retractor member 210 in a proximal direction to a position in which the sheath assembly 232 extends through cover 202 as described above.

Therefore, it can be appreciated that a locking force may be necessary to maintain the retraction assembly 230 in a distal position (e.g., a position in which cover 202 may enclose sheath assembly 232). FIG. 14 also shows retraction assembly 230 held in a distal position via actuation member 216. As shown in FIG. 14, actuation member 216 may include a projection 222 extending away from actuation member 216. Further, retractor member 210 may include a recess 220 designed to engage projection 222. When positioned as shown in FIG. 14, actuation member 216 (via projection 222) substantially prevents the proximal movement of retraction assembly 230.

Additionally, FIG. 14 illustrates that actuation member 216 may rotate about pivot point 218. Pivot point 218 may be positioned along housing assembly 201. However, it can be appreciated that pivot point 218 may be positioned such that projection 222 may engage with recess 220.

Figure 15:
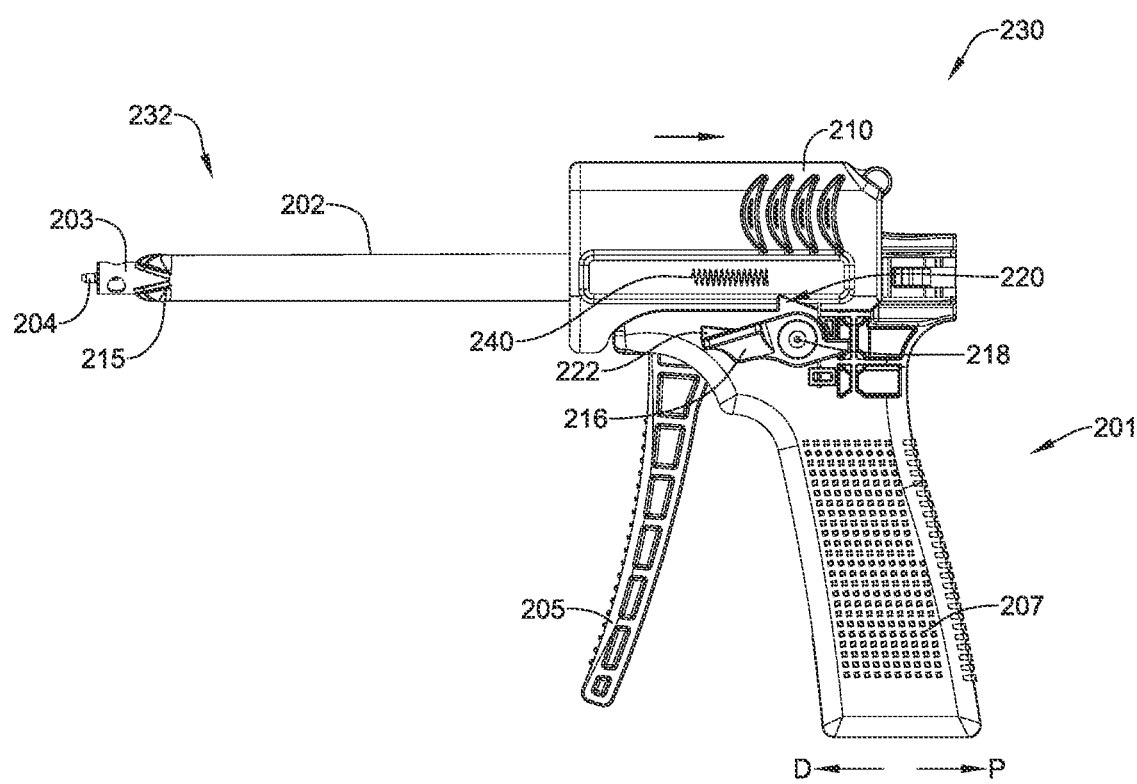
FIG. 15 is a plan view illustrating an example fastener delivery device in accordance with one example of the present disclosure.

FIG. 15 shows actuation member 216 rotated such that projection 222 disengages with recess 220. As discussed above, disengaging projection 222 from recess 220 may allow retraction assembly 230 to move from the distal position to a proximal position (in which the sheath assembly extends through cover 202 as described above). The arrow shown in FIG. 15 illustrates the movement of the retractor member 210 after the actuation member 216 is disengaged from recess 220.

Generally, components of staple delivery device 200 may be made from any rigid material. For example, in different examples, staple delivery device may be made from any of a variety of different metals or metal alloys. Some example metals include the various alloys of stainless steel. In other examples, staple delivery device 200 may be constructed from plastic. In such examples, the plastic may generally be rigid and resist deformation. Some example plastics include polymers such as Nylon 12, Polyethylene terephthalate (PET), polybutylene terephthalate (PBT), Polyamide 12, Polyether block amide (PEbax) 7233, Pebax 7033, PTFE, Polyaryletherketones (PEEK), Polyphenylene Oxide (PPO), high density polyethylene (HDPE) and the like. In still other examples, staple delivery device may be constructed from Ixef® plastics, which generally include glass fiber reinforcement in addition to one or more polymers. In still other examples, some portions of staple delivery device 200 may be constructed from plastic, such as housing 207 and trigger handle 205, and other portions of staple delivery device 200 may be constructed from metal, such as sheath 203. Of course, in other examples, other combinations of components of staple delivery device 200 may be made from plastic and metal.

Figure 16:
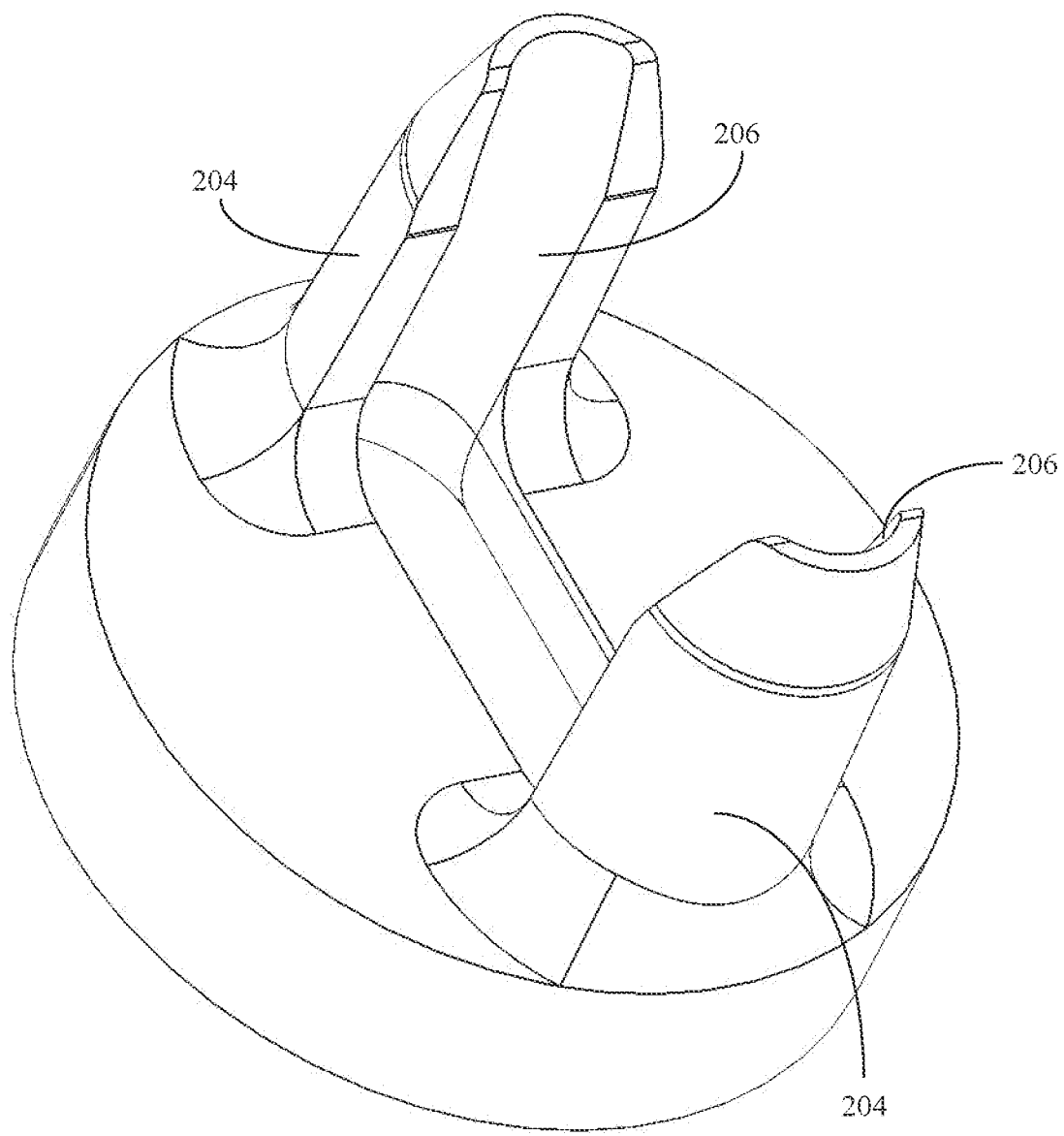
FIG. 16 is a schematic illustration depicting position retention members of an example fastener delivery device in accordance with one example of the present disclosure.

FIG. 16 depicts position retention members 204 in a close-up fashion. In some examples, position retention members 204 include curved sides 206. In such examples, curved sides of retention members 204 are configured to mate with curved sides 206 of a variety of example inserts (e.g., pilot hole forming insert 270).

As discussed above, in some examples a clinician may insert staple delivery device 200 through an access site while maintaining sheath assembly 232 (including position retention members 204) enclosed within cover 202. After positioning the cover 202 adjacent the target site, the clinician may rotate the actuation member 216, thereby disengaging projection 222 from recess 220. Furthermore, rotation of actuation member 216 may cause cover 202 to retract in a proximal direction and expose the position retention members 204. At this point, the position retention members 204 may be adjacent the target site.

Figure 17:
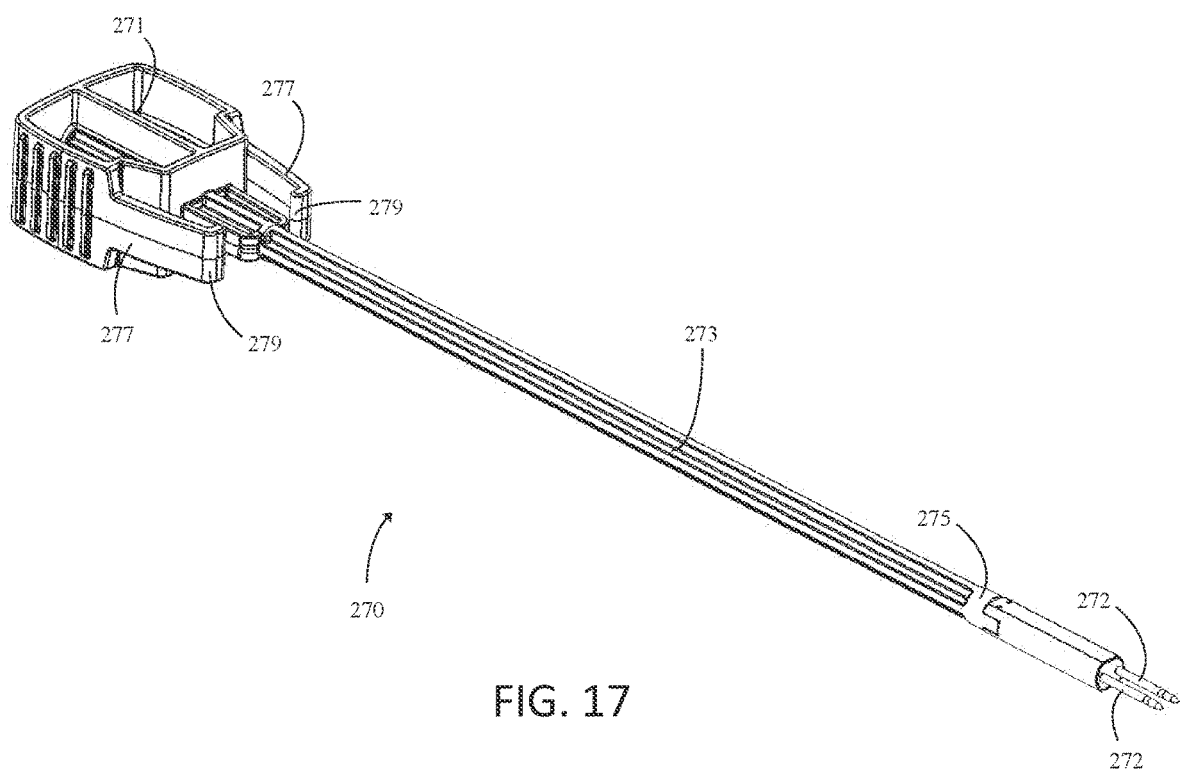
FIG. 17 is a schematic illustration depicting an example pilot hole forming insert in accordance with one example of the present disclosure.

Once portion retention members 204 are adjacent the target site, a user may insert pilot hole forming insert 270 into the lumen of sheath 203. FIG. 17 is a schematic illustration of pilot hole forming insert 270. Generally, insert 270 may have proximal head 271, shaft 273, and distal end 275. Additionally, insert 270 may have one or more pilot hole forming members 272 connected to distal end 275. In different examples, pilot hole forming members 272 may take various different shapes, such as spikes, spears, prongs, or other shapes. Whatever shape pilot hole forming members 272 may take, they may generally have pointed distal ends for piercing tissue or bone.

Insert 270 may include proximal head 271. Proximal head 270 may have connecting fins 277 extending lengthwise down insert 270 toward distal end 275. Connecting fins 277 may additionally have inward facing protrusions 279. As a user inserts insert 270 into sheath 203, inward facing protrusions 279 may slide into grooves 214, securing insert 270 to staple delivery device 200.

Figure 18:
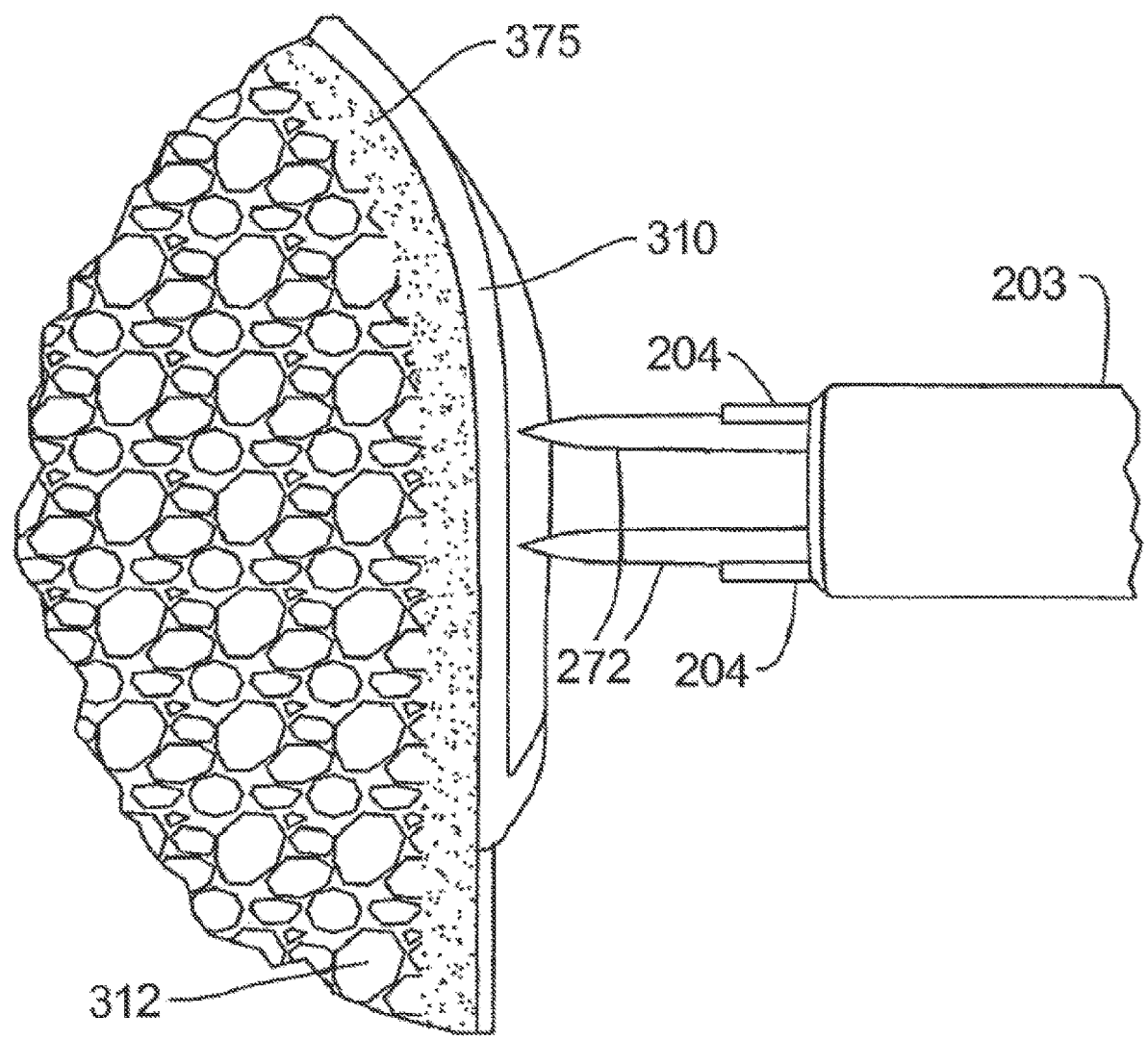
FIG. 18 is a cross section view depicting an example fastener delivery device in accordance with one example of the present disclosure positioned at an implant site.

A user may then position pilot hole forming members 272 at a location of the implant site adjacent to tissue or bone into which a staple will be deployed. FIG. 18 is a cross section illustration and depicts the implant site when sheath 203 with received insert 270 is positioned near the implant site. In FIG. 18, implant 310 can be seen positioned on top of patient tissue 312. Additionally, sheath 203 is positioned adjacent to implant 310 and patient tissue 312 with pilot hole forming members 272 extending distally of position retention members 204.

Figure 19:
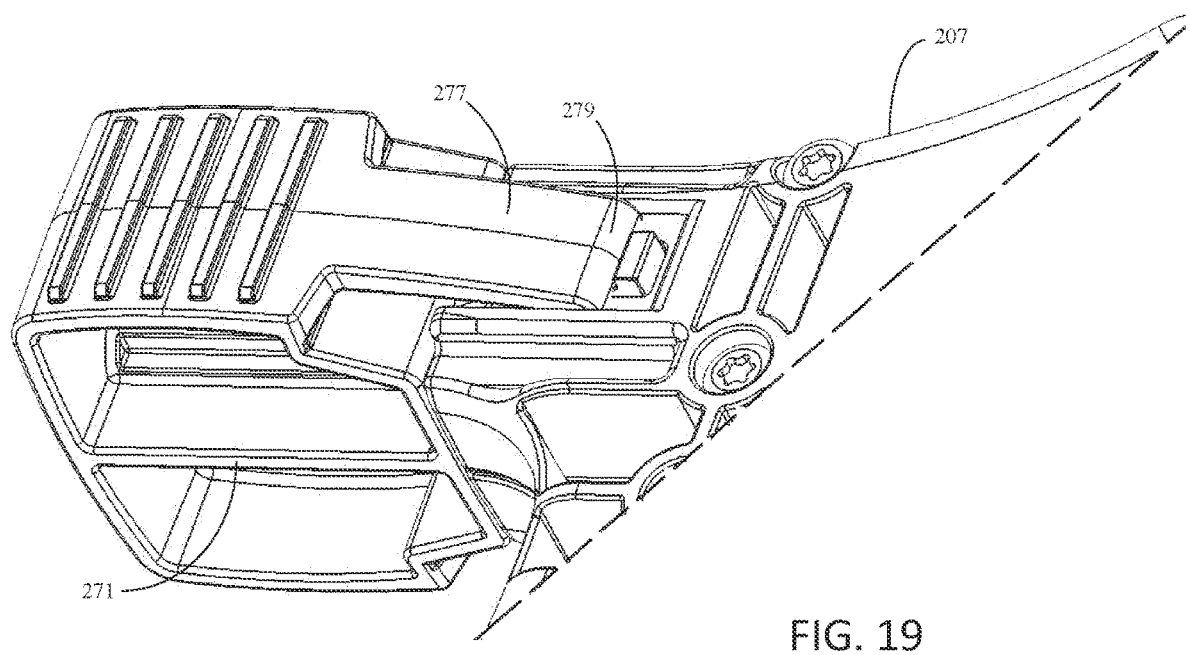
FIG. 19 is a schematic illustration depicting a proximal portion of an example fastener delivery device in accordance with one example of the present disclosure and a proximal head of an example insert when the insert is received within a sheath of the example fastener delivery device and after force has been applied to the proximal head to move the example insert in the distal direction.

Once the user has positioned pilot hole forming members 272 adjacent tissue or bone at the implant site, the user may apply a distally directed force to proximal head 271 in the distal direction. As insert 270 moves in the distal direction, pilot hole forming members 272 positioned at the implant site are driven into the tissue or bone. FIG. 19 illustrates the position of proximal head 271 with respect to housing 207 when insert 270 has been advanced in the proximal direction as far as housing 207 will allow. As depicted, no gap exists between proximal head 271 and housing 207.

Figure 20:
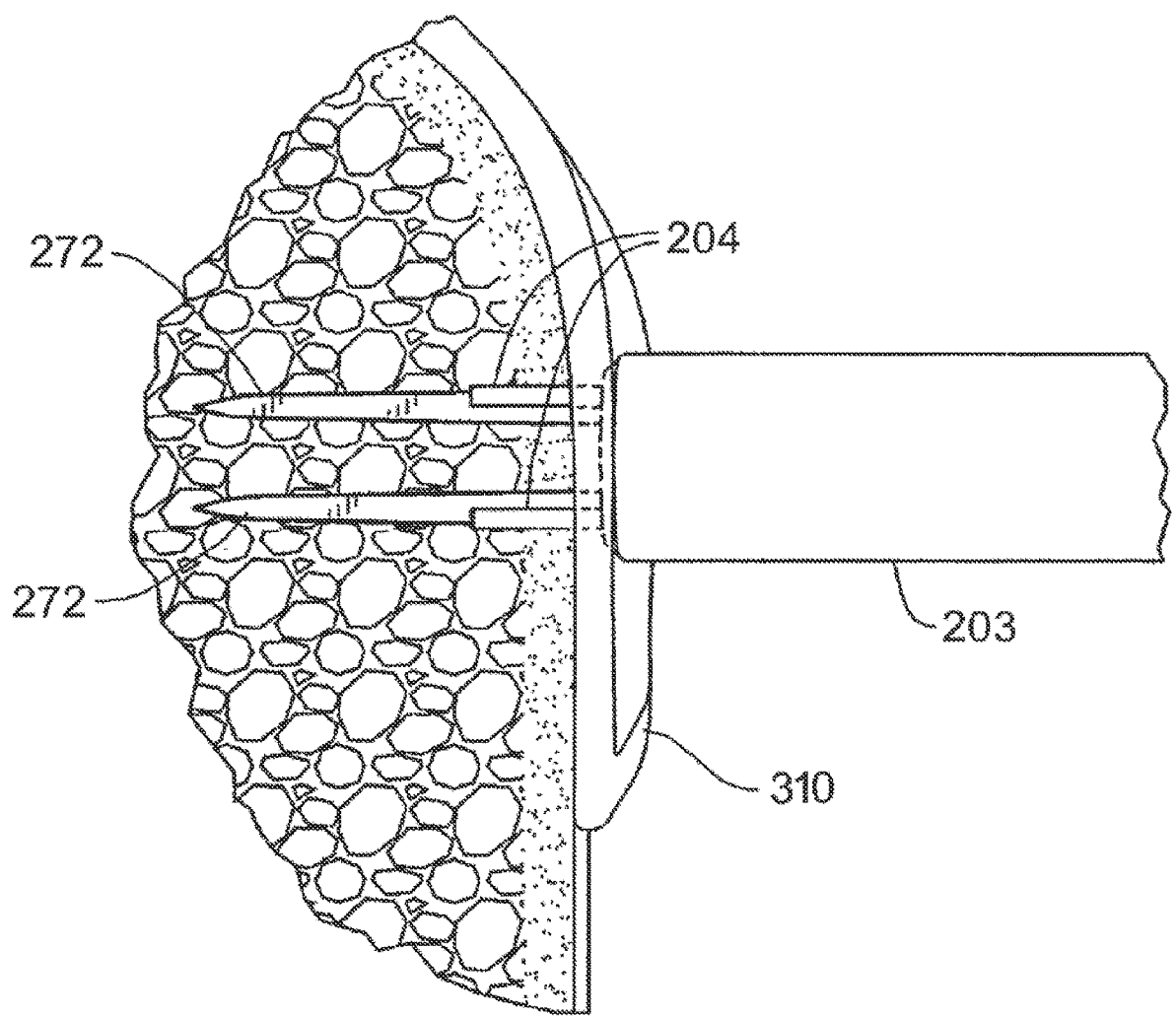
FIG. 20 is a cross section view depicting an example fastener delivery device in accordance with one example of the present disclosure positioned at an implant site after pilot hole forming members have been driven into tissue at the implant site.

FIG. 20 is another cross section illustration and depicts the position of pilot hole forming members 272 at the implant site when insert 270 has been advanced distally as far as housing 207 will allow. Pilot hole forming members can be seen extending through implant 310 and into patient tissue 312.

Another feature that staple delivery device may employ and can be seen in FIGS. 18 and 20 is the progressive disclosure of pilot hole forming members 272. That is, when inward facing protrusions 279 are engaged with grooves 214, pilot hole forming members 272 may extend distally at least partially beyond the distal end of position retention members 204. In some examples, in this initial position of proximal head 271 with respect to housing 207, pilot hole forming members 272 may extend between 0.05 inches (1.27 millimeters) and 0.35 inches (8.89 millimeters) beyond the distal end of position retention members 204, and in at least some examples, pilot hole forming members 272 may extend 0.083 inches (2.10 millimeters) beyond the distal end of position retention members 204. As force is applied to proximal head 271, and as insert 270 progresses distally, pilot hole forming members 272 extend progressively more beyond the distal end of position retention members 204. In FIG. 20, pilot hole forming members 272 are fully extended. In this position, pilot hole forming members 272 may extend between 0.4 inches (10.16 millimeters) and 0.65 inches (16.51 millimeters) beyond the distal end of position retention members 204. One advantage to examples that include this progressive disclosure feature is that having less length of pilot hole forming members 272 extending beyond position retention members 204 in the initial position may help prevent pilot hole forming members 272 from bending as force is applied to proximal head 271. In addition to driving pilot hole forming members 272 into tissue 312, the force applied to proximal head 271 may also drive position retention members 204 into tissue 312, as can be seen in FIG. 20.

Once the user has fully driven pilot hole forming members 272 into tissue 312, the user may remove insert 270. To remove insert 270, a user may squeeze trigger handle 205. Although tissue 312 may be applying squeezing forces to pilot hole forming members 272 which work to retain pilot hole forming members 272 in tissue 312, the force multiplication action of staple delivery device 200, as described previously, may assist the user in removing pilot hole forming members 272 from tissue 312.

Figure 21:
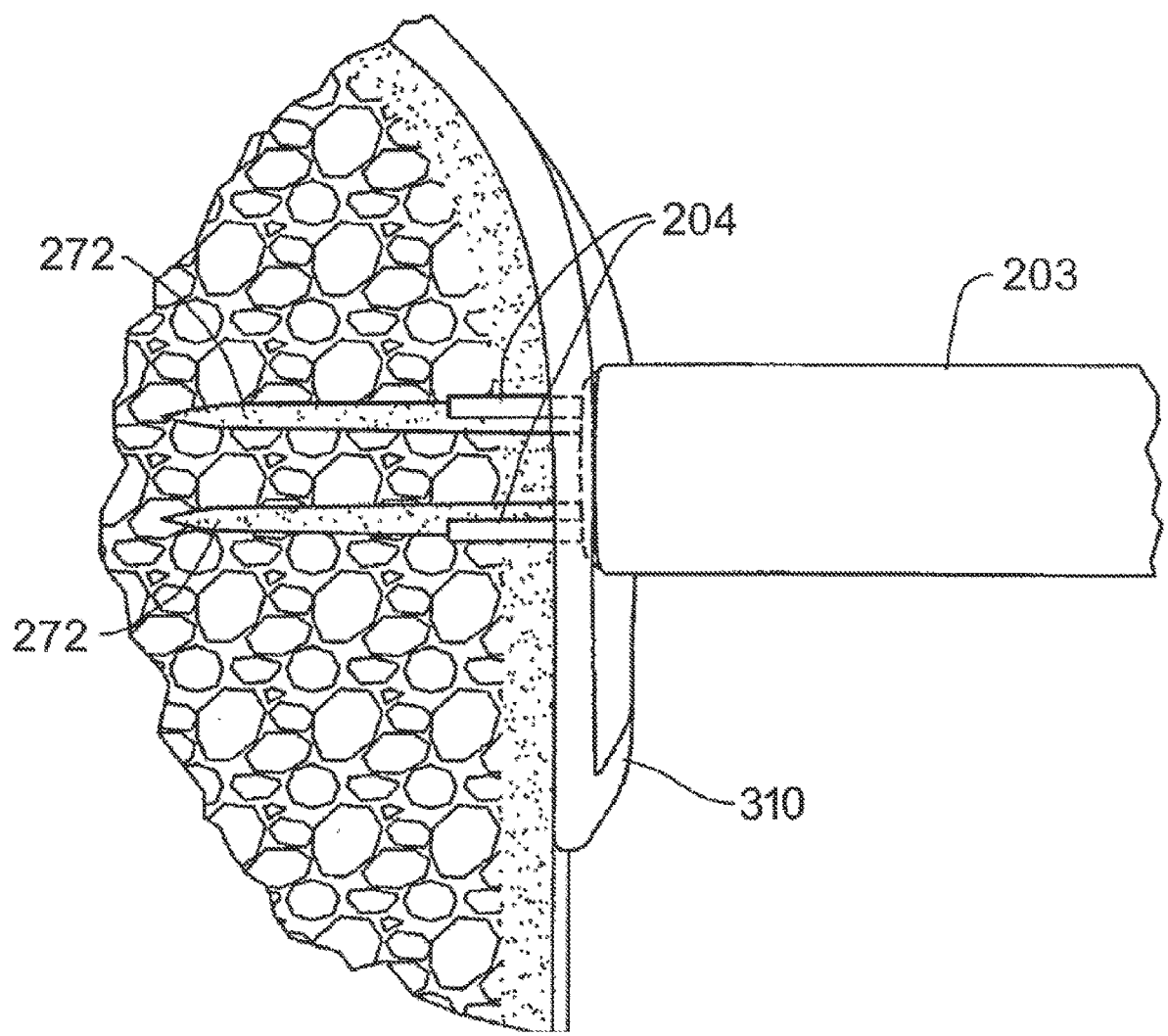
FIG. 21 is a cross section view depicting an example fastener delivery device in accordance with one example of the present disclosure positioned at an implant site after pilot hole forming members have been driven into and removed from tissue at the implant site.

FIG. 21 is another cross section illustration that depicts the implant area once insert 270 has been removed from staple delivery device 200. FIG. 21 illustrates that even after insert 270 has been removed, position retention members 204 may still remain in tissue 312. Position retention members 204 may act to maintain sheath 203 in position with respect to pilot holes 309 left by the pilot hole forming members 272.

Figure 22:
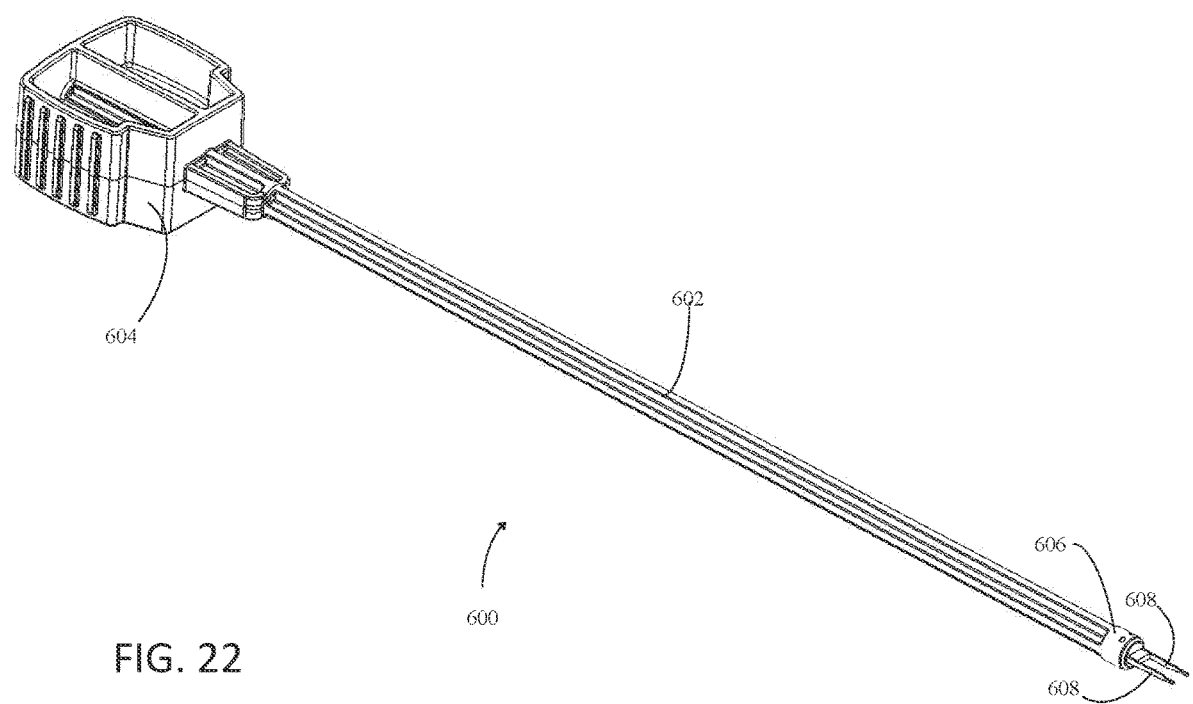
FIG. 22 is a schematic illustration depicting an example staple delivery insert in accordance with one example of the present disclosure.
Figure 23:
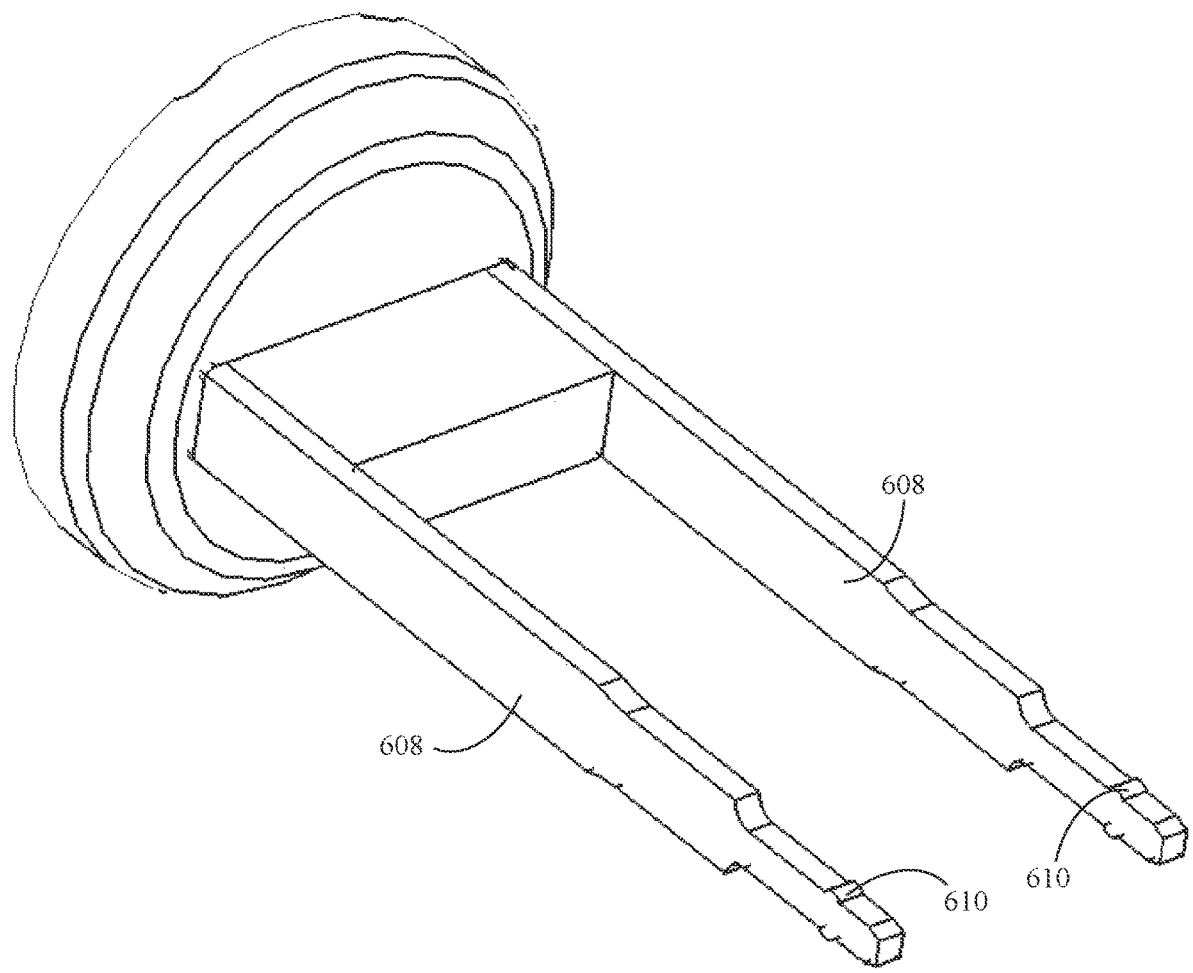
FIG. 23 is a schematic illustration of a distal portion of an example staple delivery insert in accordance with one example of the present disclosure.

Next, a user may insert staple delivery insert 600, as depicted in FIG. 22, into staple delivery device 200. Again, staple delivery insert 600 may generally be similar to insert 270. For instance, insert 600 may be comprised of shaft 602, proximal head 604, and distal end 606. However, staple delivery insert 600 may have arms 608 connected to distal end 606 which may retain a staple, such as staple 100. In some examples, arms 608 may include detents 610, as illustrated in FIG. 23. Arms 608 may be designed to be received into cavities 128A, 128B of staple 100 and retain staple 100 with friction. For instance, when arms 608 are received within cavities 128A, 128B of staple 100, detents 610 may press against inner surfaces of cavities 128A, 128B, thereby retaining staple 100 to arms 608 by friction. Once staple delivery insert 600 is received within sheath 203, a user may then apply force to the proximal end of staple delivery insert 600. The applied force may drive arms 610 of the staple delivery device, along with retained staple 100, into pilot holes 309. As discussed with respect to FIGS. 1-4, natural movement of tissue 312 and/or a pullout force applied to the bridge of staple 100 may act to secure staple 100 within tissue 312.

Figure 24:
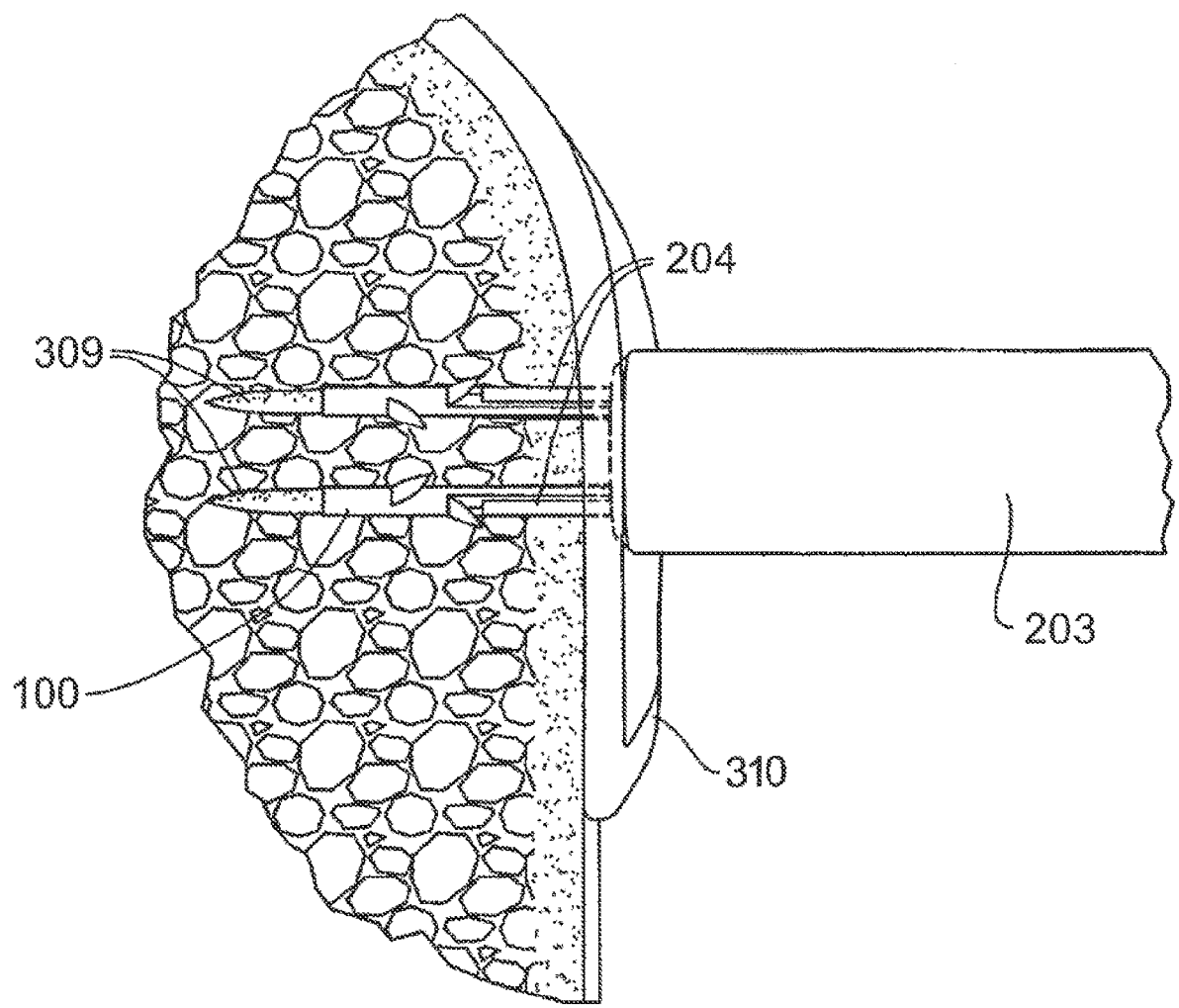
FIG. 24 is a cross section view depicting an example fastener delivery device in accordance with one example of the present disclosure positioned at an implant site after an example fastener has been deployed into pilot holes formed in tissue at the implant site.

The user may then remove staple delivery insert 600 from staple delivery device 200. Tissue 312 may impart a holding force on staple 100 sufficient to overcome the friction force between detents 610 on arms 608 of staple delivery insert 600 and staple 100 such that staple delivery insert 600 may be removed from tissue 312 while staple 100 remains in tissue 312, as depicted in FIG. 24.

Finally, the user may then retract staple delivery device 200 from the patient and finish the procedure to secure implant 310 to tissue 312 of the patient. This may include fixing staple 100 to a tendon of the patient with one or more fixation devices. Alternatively, implant 310 may have already been affixed to the tendon before affixing implant 310 to tissue 312.

In light of the above description, it should be understood that other examples of staple 100, staple delivery device 200, and insert 270 that are still within the spirit and scope of the present disclosure may differ from the specific examples illustrated herein.

Accordingly, it should be generally understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A fastener delivery tool, comprising:
    a sheath assembly including a tubular sheath and one or more position retention members;
    a retraction assembly including a cover and a retractor member, which move in unison between a first position of the retraction assembly and a second position of the retraction assembly, wherein the cover includes a lumen extending therein;
    a handle assembly coupled to a proximal end of the sheath assembly, the handle assembly including a housing fixed to a proximal end of the sheath and an actuation member, the actuation member including a projection configured to engage with a recess disposed along the retractor member;
    wherein the sheath assembly extends through the lumen of the cover; and
    wherein actuation of the actuation member moves the retractor assembly along the housing of the handle assembly from the first position to the second position, wherein the retractor member is configured to move relative to the housing between the first position of the retraction assembly in which the sheath assembly is disposed within a distal portion of the cover and the second position of the retraction assembly in which the sheath assembly extends out of the distal portion of the cover.

2. The fastener delivery tool of claim 1, wherein the actuation member is designed to rotate relative to the housing.

3. The fastener delivery tool of claim 1, wherein actuation of the actuation member rotates the actuation member about an attachment point disposed along the housing, and wherein rotation of the actuation member about the attachment point is designed to disengage the projection from the recess.

4. The fastener delivery tool of claim 1, wherein the one or more position retention members fixedly extend from a distal end of the tubular sheath to maintain a position of the tubular sheath at a target site.

5. The fastener delivery tool of claim 1, wherein the retraction assembly is biased to be in the second position.

6. The fastener delivery tool of claim 1, further comprising a spring coupled to the retractor member.

7. The fastener delivery tool of claim 6, wherein the spring shifts the retractor member from the first position to the second position when the actuation member is actuated.

8. The fastener delivery tool of claim 1, wherein the cover includes one or more leaflets positioned on a distal portion thereof.

9. The fastener delivery tool of claim 8, wherein at least one of the one or more leaflets includes a proximal portion and a distal portion, and wherein at least one of the one or more leaflets are tapered from the proximal portion to the distal portion.

10. The fastener delivery tool of claim 8, wherein the one or more leaflets are biased in a closed position.

11. The fastener delivery tool of claim 8, wherein the one or more leaflets are configured to expand radially outward as the retraction assembly slides from the first position to the second position.

12. The fastener delivery tool of claim 1, wherein shifting the retractor member between the first position and the second position uncovers the sheath assembly in vivo.

13. The fastener delivery tool of claim 1, wherein a proximal portion of the cover is attached to the retractor member.

14. A fastener delivery tool, comprising:
    a handle assembly including a housing, a retractor member and an actuation member; and
    a sheath assembly including a sheath, a cover and a position retention member;
    wherein the sheath extends within a lumen of the cover;
    wherein a proximal portion of the sheath assembly is coupled to the handle assembly;
    wherein the actuation member includes a projection configured to engage with a recess disposed along the retractor member;
    wherein actuation of the actuation member slides the retractor member from a first position in which the sheath assembly is disposed within a distal portion of the cover to a second position in which the sheath assembly extends out of the distal portion of the cover.

15. The fastener delivery tool of claim 14, wherein actuation of the actuation member rotates the actuation member about an attachment point disposed along the housing, and wherein rotation of the actuation member about the attachment point is designed to disengage the projection from the recess.

16. The fastener delivery tool of claim 14, wherein the retractor member is biased to be in the second position.

17. The fastener delivery tool of claim 14, wherein the cover includes one or more leaflets positioned on a distal portion of the cover.

18. A method for deploying a fastener, the method comprising:
   positioning a fastener delivery tool adjacent a target site, the fastener delivery tool comprising:
   a sheath assembly including a sheath and a position retention member;
   a retraction assembly including a cover and a retractor member, wherein the cover includes a lumen extending therein; and
   a handle assembly coupled to a proximal end of the sheath assembly, the handle assembly including a housing, a trigger and an actuation member;
   wherein the sheath assembly extends through the lumen of the cover;
   actuating the actuation member to move the retractor member from a first position in which the sheath assembly is disposed within a distal portion of the cover to a second position in which the sheath assembly extends out of the distal portion of the cover, wherein the actuation member includes a projection configured to engage with a recess disposed along the retractor member; and
   deploying a staple along a target site.

* * * * *